United States Patent
Marotta

(10) Patent No.: US 10,746,710 B2
(45) Date of Patent: Aug. 18, 2020

(54) DEVICES, SYSTEMS AND METHODS FOR ANALYZING FLUID STREAMS

(71) Applicant: Lee Marotta, North Bergen, NJ (US)

(72) Inventor: Lee Marotta, North Bergen, NJ (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 699 days.

(21) Appl. No.: 14/209,128

(22) Filed: Mar. 13, 2014

(65) Prior Publication Data

US 2014/0345370 A1    Nov. 27, 2014

Related U.S. Application Data

(60) Provisional application No. 61/784,003, filed on Mar. 14, 2013.

(51) Int. Cl.

| | |
|---|---|
| *G01N 30/88* | (2006.01) |
| *B01D 15/00* | (2006.01) |
| *G01N 33/22* | (2006.01) |
| *G01N 1/22* | (2006.01) |
| *G01N 30/12* | (2006.01) |
| *B01J 20/281* | (2006.01) |
| *G01N 33/00* | (2006.01) |
| *G01N 1/40* | (2006.01) |

(52) U.S. Cl.
CPC ........... *G01N 30/88* (2013.01); *B01D 15/00* (2013.01); *G01N 1/2214* (2013.01); *G01N 30/12* (2013.01); *G01N 30/482* (2013.01); *G01N 33/225* (2013.01); *G01N 1/405* (2013.01); *G01N 33/0021* (2013.01); *G01N 2030/126* (2013.01); *G01N 2030/8854* (2013.01)

(58) Field of Classification Search
CPC ................ G01N 30/88; G01N 30/482; G01N 2030/8854; G01N 33/225; G01N 33/0021; G01N 1/405; G01N 30/12; G01N 2030/126; B01D 15/00
USPC ........................................................ 73/61.55
See application file for complete search history.

(56) References Cited

U.S. PATENT DOCUMENTS

| | | | |
|---|---|---|---|
| 6,649,129 | B1 | 11/2003 | Neal |
| 2009/0018668 | A1 | 1/2009 | Galbraith |
| 2010/0068821 | A1 | 3/2010 | St German |
| 2010/0242579 | A1 | 9/2010 | Tipler |

OTHER PUBLICATIONS

ISR/IPRP for PCT/US14/26052 dated Jul. 18, 2014.

*Primary Examiner* — Rebecca M Fritchman
(74) *Attorney, Agent, or Firm* — Rhodes IP PLC; Christopher R Rhodes

(57) ABSTRACT

Certain embodiments described herein are directed to systems and methods that can be used to analyze species in a fluid stream. In some configurations, a sorbent tube effective to directly sample aromatics and/or polyaromatics in a fluid stream is described.

16 Claims, 12 Drawing Sheets

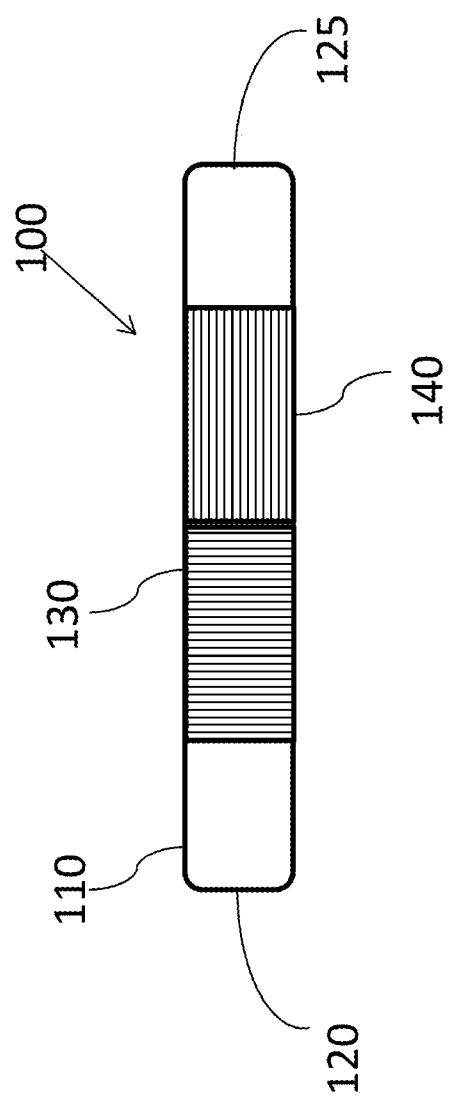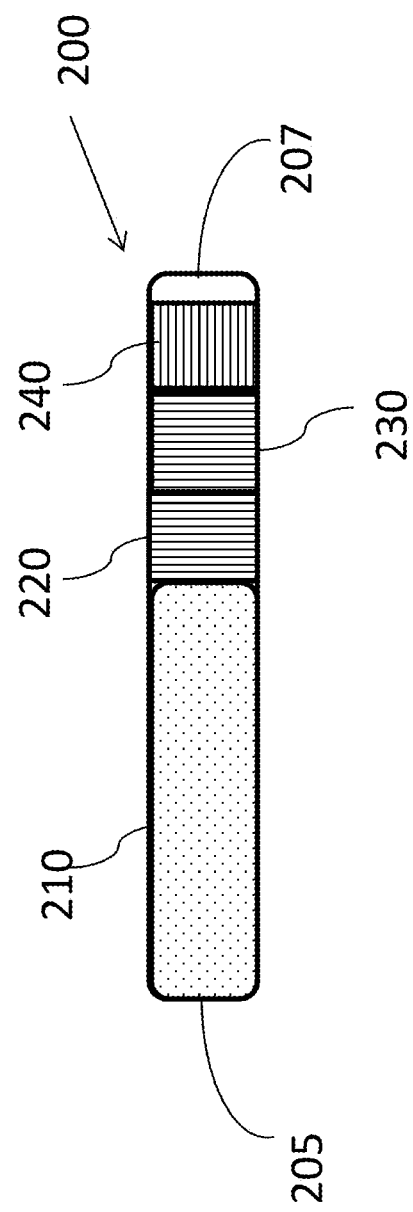

DEVICES, SYSTEMS AND METHODS FOR ANALYZING FLUID STREAMS

PRIORITY APPLICATION

This application is related to, and claims the benefit of, U.S. Provisional Application No. 61/784,003 filed on Mar. 14, 2013, the entire disclosure of which is hereby incorporated herein by reference for all purposes.

TECHNOLOGICAL FIELD

This application is related to devices, methods and systems that can be used to analyze fluid streams. More particularly, certain embodiments described herein are directed to devices and methods configured to analyze aromatic and polyaromatic hydrocarbons or soluble residue in fluid streams.

BACKGROUND

Liquefied petroleum gas generally comprises many different hydrocarbons. Residue in the liquefied petroleum gas can lead to operation problems even where residue levels are as low as 10 mg/kg.

SUMMARY

Certain features, aspects and embodiments described herein are directed to systems that are configured to sample various fluid streams, e.g., air streams comprising aromatic and polyaromatic hydrocarbons or liquefied petroleum gas streams. In some configurations, the system can include integral features to separate and/or analyze the residue in the liquefied petroleum gas streams.

In one aspect, a method of analyzing residue in liquefied petroleum gas, the method comprising introducing a liquid stream comprising liquefied petroleum gas into a sample loop to load the sample loop with the liquid stream, introducing the loaded, liquid stream into a sorbent tube effective to permit passage of substantially all the liquefied petroleum gas and effective to adsorb residue that is soluble in the liquid petroleum from the liquid stream, desorbing the adsorbed residue from the sorbent tube, and detecting residue species of the desorbed residue is provided.

In certain embodiments, the method may comprise desorbing the adsorbed components from the sorbent tube by heating the sorbent tube with an inert gas flowing through the tube at the same time. In other embodiments, the method may comprise condensing the desorbed components prior to separation of the desorbed components by chromatography. In additional examples, the method may comprise vaporizing the condensed components. In other examples, the method may comprise separating the vaporized components using chromatography. In further embodiments, the method may comprise sequentially detecting each of the separated, desorbed components to determine the amount of residue in the liquid stream comprising the liquefied petroleum gas. In other examples, the method may comprise introducing the loaded, liquid stream to the sorbent tube at an effective pressure to vaporize the liquid stream in the sorbent tube. In some examples, the method may comprise monitoring the temperature of the sorbent tube to determine if vaporization of the liquid stream in the sorbent tube occurs. In additional examples, the method may comprise condensing a fluid stream to provide the liquid stream prior to introduction into the sorbent tube. In some examples, the method may comprise determining if the total adsorbed species are below a threshold value.

In another aspect, a sorbent tube effective to retain soluble residue in a liquid stream comprising liquefied petroleum gas is described. In some embodiments, the sorbent tube comprises a body comprising an inlet and an outlet, and an effective amount of each of a plurality of sorbent materials disposed within the body, the plurality of sorbent materials together effective to permit passage of substantially all liquefied petroleum gas in the liquid stream and to reversibly adsorb substantially all soluble residue components in the liquid stream comprising the liquefied petroleum gas.

In certain embodiments, the sorbent tube comprises at least three different materials. In some instances, at least one of the materials is effective to provide a condensation surface without substantial absorbance to the material. In other embodiments, at least one of the three different materials comprise glass beads, glass wool, glass particles or combinations thereof. In further embodiments, one of three different materials is glass beads. In some examples, one of the three different materials is glass beads and the other two materials are different graphitized carbon black sorbent materials. In certain examples, the sorbent materials are effective to reversibly adsorb soluble residue comprising at least six carbon atoms. In some examples, the sorbent materials are effective to reversibly adsorb soluble residue comprising up to forty-four carbon atoms. In certain examples, the sorbent materials are effective to permit passage of components in the liquefied petroleum gas that comprises five or fewer carbon atoms. In other embodiments, the sorbent tube may comprise a temperature jacket thermally coupled to the body of the sorbent tube. In some embodiments, the sorbent tube can include an expansion chamber within the sorbent tube between an inlet of the sorbent tube and the first sorbent material in the body of the sorbent tube. In some examples, the sorbent tube may comprise at least three different materials, in which the materials are packed between the expansion chamber and an outlet of the body. In certain examples, at least one of the three different materials comprises glass beads, glass wool, glass particles or combinations thereof. In some examples, one of the three different materials is glass beads. In other examples, one of the three different materials is glass beads and the other two materials are different graphitized carbon black sorbent materials. In some embodiments, the expansion chamber comprises a plurality of fins.

In other embodiments, the sorbent tube with the expansion chamber may comprise at least three different materials, in which the materials are packed between the expansion chamber and an outlet of the body. In some embodiments, at least one of the three different materials at least one of the materials is effective to provide a condensation surface without substantial absorbance to the material, e.g., comprises glass beads, glass wool, glass particles or combinations thereof. In some examples, one of the three different materials is glass beads and the other two materials are different graphitized carbon black sorbent materials. In some embodiments, the sorbent tube with the expansion chamber may comprise a temperature jacket thermally coupled to the body of the sorbent tube In an additional aspect, a sampling cell comprising a sample loop comprising an inlet and an outlet, the sample loop configured to fluidically couple to a sample introduction system at the inlet and a sorbent tube at the outlet is disclosed. In certain examples, the sampling cell is further configured to provide an effective pressure to maintain a liquid stream comprising liquefied petroleum gas and residue soluble in the liquefied petroleum gas in the liquid state in the sample loop.

In another aspect, a system comprising a sample introduction system fluidically coupled to a sorbent tube is provided. In some embodiments, the sorbent tube of the system can be configured to permit introduction of a liquefied petroleum gas and residue into the sorbent tube. In some embodiments, the system can also include a detector fluidically coupled to the sampling system is described.

In certain examples, the detector is selected from the group consisting of a flame ionization detector (FID), a flame photometric detector (FPD), a thermal conductivity detector (TCD), a thermionic detector (TID), an electron-capture detector (ECD), an atomic emission detector (AED), a photoionization detector (PID), an infrared detector, or other detectors commonly used with gas chromatography. In addition, the detector may be a mass spectrometer, an external detector such as, for example, a discharge ionization detector (DID) or a sulfur chemiluminescence detector (SCD) or other suitable detectors and devices that can be hyphenated to a gas chromatography device or other fluid chromatography devices, e.g., those using capillary columns.

In an additional aspect, an in-line liquefied petroleum gas residue filter comprising a body effective to receive at least one sorbent material, the body comprising a first coupler configured to fluidically couple the body to a source of liquefied petroleum gas, and a plurality of sorbent materials disposed within the body, the plurality of sorbent materials together effective to permit passage of substantially all liquefied petroleum gas and to adsorb substantially all soluble, residue components in the liquefied petroleum gas is provided.

In certain examples, at least one of the plurality of materials comprises a material effective to provide a condensation surface without substantial absorbance to the material, e.g., glass beads, glass wool, glass particles or combinations thereof. In some examples, the body is configured as a canister comprising a plurality of channels, in which each channel comprises a plurality of sorbent materials disposed within the channel, the plurality of sorbent materials together effective to permit passage of substantially all liquefied petroleum gas and to adsorb substantially all soluble, residue components in the liquefied petroleum gas. In some embodiments, the filter may comprise an expansion chamber in the body. In other embodiments, the body is configured as a canister comprising a plurality of channels, in which each channel is configured to receive a removable filter comprising the plurality of sorbent materials disposed within the filter, the plurality of sorbent materials together effective to permit passage of substantially all liquefied petroleum gas and to adsorb substantially all soluble, residue components in the liquefied petroleum gas. In some examples, the filter comprises an expansion chamber in the body. In other examples, at least one of the materials comprises glass beads, glass wool, glass particles or combinations thereof. In additional examples, the filter comprises at least two different sorbent materials which are different graphitized carbon black sorbent materials. In further examples, at least one of the sorbent materials is glass beads. In some examples, the filter comprises an expansion chamber in the body, in which the expansion chamber is between an inlet of the body and the plurality of sorbent materials.

In another aspect, a system comprising an engine, a fuel source comprising liquefied petroleum gas, and an in-line gas residue filter between the engine and the fuel source, the in-line gas residue filter comprising a plurality of sorbent materials together effective to permit passage of a substantially all liquefied petroleum gas components in a fluid stream and to adsorb substantially all soluble, residue components in the liquefied petroleum gas of the fluid stream is disclosed.

In certain examples, the system can include a regulator between the fuel source and the engine, the regulator configured to permit vaporization of the liquefied petroleum gas prior to introduction into the engine. In some examples, the in-line gas residue filter comprises an expansion chamber to permit operation of the system without the use of a regulator. In other embodiments, the in-line gas residue filter is configured as a canister comprising a plurality of channels, in which each channel comprises a plurality of sorbent materials disposed within the channel, the plurality of sorbent materials together effective to permit passage of substantially all liquefied petroleum gas and to adsorb substantially all soluble, residue components in the liquefied petroleum gas. In some examples, the system can include an expansion chamber between an inlet of the gas residue filter and the sorbent materials. In certain examples, the in-line gas residue filter is configured as a canister comprising a plurality of channels, in which each channel is configured to receive a removable filter comprising the plurality of sorbent materials disposed within the filter, the plurality of sorbent materials together effective to permit passage of substantially all liquefied petroleum gas and to adsorb substantially all soluble, residue components in the liquefied petroleum gas. In some embodiments, the system can include an expansion chamber between an inlet of the gas residue filter and the sorbent materials. In some examples, at least one of the materials comprises glass beads, glass wool, glass particles or combinations thereof. In other examples, the system can include at least two different materials which are different graphitized carbon black sorbent materials.

In an additional aspect, a system comprising a burner, a fuel source comprising liquefied petroleum gas, and an in-line gas residue filter between the burner and the fuel source, the in-line gas residue filter comprising a plurality of sorbent materials together effective to permit passage of a substantially all liquefied petroleum gas components in a fluid stream and to adsorb substantially all soluble residue components in the liquefied petroleum gas of the fluid stream is described.

In certain embodiments, the system can include a regulator between the fuel source and the burner, the regulator configured to permit vaporization of the liquefied petroleum gas prior to introduction into the burner. In some embodiments, the in-line gas residue filter comprises an expansion chamber to permit operation of the system without the use of a regulator. In further examples, the in-line gas residue filter is configured as a canister comprising a plurality of channels, in which each channel comprises a plurality of sorbent materials disposed within the channel, the plurality of sorbent materials together effective to permit passage of substantially all liquefied petroleum gas and to adsorb substantially all soluble, residue components in the liquefied petroleum gas. In certain examples, the system can include an expansion chamber between an inlet of the gas residue filter and the sorbent materials. In some examples, the in-line gas residue filter is configured as a canister comprising a plurality of channels, in which each channel is configured to receive a removable filter comprising the plurality of sorbent materials disposed within the filter, the plurality of sorbent materials together effective to permit passage of substantially all liquefied petroleum gas and to adsorb substantially all soluble, residue components in the liquefied petroleum gas. In other examples, the system comprises an expansion chamber between an inlet of the gas residue filter and the sorbent materials. In some examples, at least one of the materials comprises glass beads, glass wool, glass particles or combinations thereof. In other examples, at least two different sorbent materials are present which are different graphitized carbon black sorbent materials.

In another aspect, a method of analyzing benzene/toluene/ethyl benzene/xylenes (BTEX) and including, for example, the 16 EPA regulated polynuclear aromatic hydrocarbons (PAHs) and/or other PAHs in a fluid sample, e.g., in ambient air, introducing a fluid sample, e.g., using a high precision pump, introducing the loaded, liquid stream into a sorbent tube effective to adsorb BTEX and PAHs that are present in the liquid stream, desorbing the adsorbed BTEX and PAHs from the sorbent tube, and detecting the BTEX and PAHs. In some embodiments, compounds with six carbons to about 44 carbons can be analyzed. The air can be sampled onto the sorbent tube using a pump at a known flow rate for a known amount of time to permit quantitation. In some instances, direct sampling of the air or fluid stream can be performed to permit analysis of C6 to C44 materials (or C4 to C44 materials) in the air or fluid stream, e.g., no cartridge or other device is used prior to loading the air or fluid stream onto the sorbent tube. In instances where the fluid stream takes the form of a gas comprising C6 to C44 species (or C4 to C44 species), the gas may be loaded directly onto the tube without any liquid extraction or other pre-tube loading procedures.

In certain embodiments, the method comprises desorbing the adsorbed components from the sorbent tube by heating the sorbent tube, e.g., heating the tube with an inert gas flowing through the tube. In other embodiments, the method comprises condensing the desorbed components prior to separation of the desorbed components by chromatography. In further embodiments, the method comprises vaporizing the condensed components. In additional embodiments, the method comprises separating the vaporized components using chromatography. In further examples, the method comprises sequentially detecting each of the separated, desorbed components to determine the amount of BTEX and PAHs in the fluid stream or sample. In additional examples, the method comprises monitoring the temperature of the sorbent tube. In additional examples, the method comprises determining if the total adsorbed species are below a threshold value.

In an additional aspect, a sorbent tube effective to retain BTEX and PAHs present in a fluid stream, e.g., an air stream or air sample, the sorbent tube comprising a body comprising an inlet and an outlet, and an effective amount of each of a plurality of sorbent materials disposed within the body, the plurality of sorbent materials together to reversibly adsorb substantially all BTEX and PAHs in the liquid stream. In certain examples, the sorbent tube may comprise at least three different materials. In other examples, at least one of the three different materials is effective to provide a condensation surface without substantial absorbance to the material, e.g., comprises glass beads, glass wool, glass particles or combinations thereof. In some examples, one of the three different materials is glass beads. In other examples, one of the three different materials is glass beads and the other two materials are different graphitized carbon black sorbent materials. In further examples, the sorbent materials are effective to reversibly adsorb substantially all the BTEX and PAHs. In some embodiments, the sorbent materials are effective to reversibly adsorb substantially all the BTEX and PAHs with six or more carbon atoms. In some instances, the sorbent materials are effective to permit simultaneous analysis of BTEX and PAHs in a single desorption cycle. In other examples, the sorbent materials are effective to reversibly adsorb substantially all the BTEX and PAHs when the sorbent tube comprises at least three different materials with one of the three different materials comprising glass beads.

In other examples, the sorbent tube can include a temperature jacket thermally coupled to the body of the sorbent tube. In some embodiments, the sorbent tube can include an expansion chamber within the sorbent tube between an inlet of the sorbent tube and the first sorbent material in the body of the sorbent tube. In additional embodiments, the sorbent tube can include at least three different materials, in which the materials are packed between the expansion chamber and an outlet of the body. In some examples, at least one of the three different materials comprises glass beads. In some embodiments, one of the three different sorbent materials is glass beads. In other examples, one of the three different materials is glass beads and the other two sorbent materials are different graphitized carbon black sorbent materials. In some embodiments, the expansion chamber comprises a plurality of fins. In further embodiments, at least three different sorbent materials, in which the sorbent materials are packed between the expansion chamber and an outlet of the body. In some examples, at least one of the three different sorbent materials comprises glass beads. In certain examples, one of the three different sorbent materials is glass beads. In some embodiments, one of the three different sorbent materials is glass beads and the other two sorbent materials are different graphitized carbon black materials. In certain examples, the sorbent tube can include a temperature jacket thermally coupled to the body of the sorbent tube.

In another aspect, a pump can be used to sample ambient air in the direction from weaker to stronger adsorbent so that the higher boiling material does not enter the strong adsorbent but is adsorbed to the weak adsorbent under ambient conditions.

In an additional aspect, a method of analyzing a fluid stream, e.g., a gas stream, comprising C4 to C44 components without any liquid extraction steps, the method comprising introducing the gas stream directly into a sorbent tube effective to reversibly adsorb C4 to C44 species, desorbing the adsorbed components from the sorbent tube, and detecting the desorbed components is provided.

In certain embodiments, the method comprises desorbing the adsorbed components from the sorbent tube by heating the sorbent tube. In other embodiments, the method comprises condensing the desorbed components prior to separation of the desorbed components by chromatography. In additional examples, the method comprises vaporizing the condensed components. In further examples, the method comprises separating the vaporized components using chromatography. In some embodiments, the method comprises sequentially detecting each of the separated, desorbed components to determine the amount of C4 to C44 components in the gas stream. In certain instances, the gas stream is ambient air. In some embodiments, the method comprises heating the sorbent tube during the desorption step. In further embodiments, the method comprises introducing a carrier gas as a reverse flow during the desorption step. In additional embodiments, the method comprises introducing the gas stream without any liquid extraction or canister capture of the gas stream prior to the introducing step.

In some embodiments, a sorbent tube effective to reversibly adsorb C4 to C44 species in a fluid stream, the sorbent tube comprising a body comprising and inlet and an outlet, and an effective amount of each of a plurality of materials disposed within the body, the plurality of materials together effective to reversibly adsorb the C4 to C44 species in the fluid stream is described. In certain examples, the sorbent tube may comprise at least two different sorbent materials. In other embodiments, at least one of the plurality of materials comprises glass beads, glass wool, glass particles and combinations thereof. In other configurations, one of the materials is glass beads and the other two materials are different graphitized carbon black sorbent materials. In some examples, the materials are effective to reversibly adsorb substantially all the C4 to C44 species in the fluid stream without any breakthrough. In other embodiments, the materials are effective to permit simultaneous analysis of C4 to C44 species in a single desorption cycle. In further examples, the sorbent tube may comprise a temperature jacket thermally coupled to the body of the sorbent tube. In other example, the sorbent tube may comprise an expansion chamber within the sorbent tube between an inlet of the sorbent tube and a first material in the body of the sorbent tube. In additional embodiments, at least three different materials may be present in the sorbent tube, in which the materials are packed between the expansion chamber and an outlet of the body. In further configurations, at least one of the three different materials comprises glass beads, glass wool, glass particles and combinations thereof. In some instances, the plurality of materials together are effective to sample an gas stream comprising the C4 to C44 species by direct sampling of the gas stream onto the sorbent tube without substantial breakthrough of any of the C4 to C44 species in the gas stream. In further examples, the sorbent materials are effective to permit the direct sampling without any liquid extraction prior to loading of the gas stream on the sorbent tube. In other embodiments, the materials together are effective to permit the direct sampling without sampling of the gas stream onto a canister.

Additional features, aspect, examples and embodiments are described in more detail below.

BRIEF DESCRIPTION OF THE FIGURES

Certain embodiments are described with reference to the accompanying figures in which:

FIG. 1 is an illustration of a sorbent tube, in accordance with certain examples;

FIG. 2 is an illustration of a sorbent tube comprising an expansion chamber, in accordance with certain examples;

Figure 3:
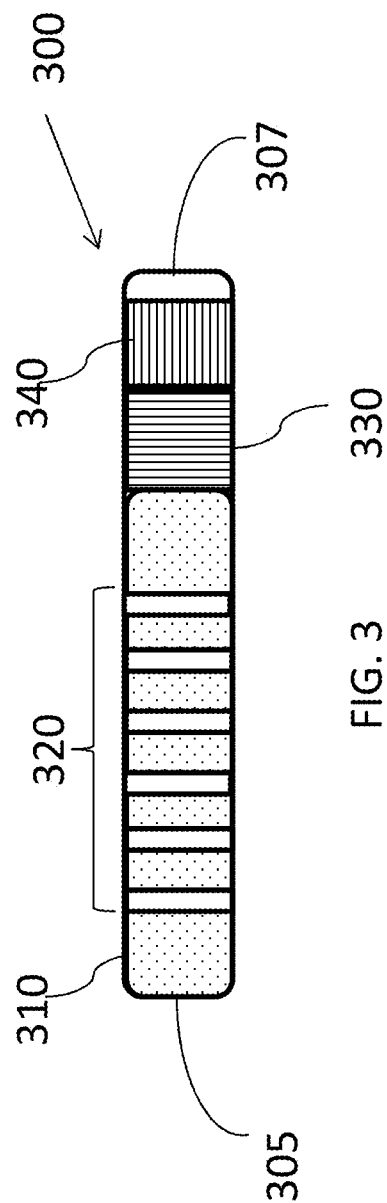
FIG. 3 is an illustration of a sorbent tube comprising an expansion chamber with fins, in accordance with certain examples.

It will be recognized by the person of ordinary skill in the art, given the benefit of this disclosure, that certain dimensions or features of the components of the systems may have been enlarged, distorted or shown in an otherwise unconventional or non-proportional manner to provide a more user friendly version of the figures.

DETAILED DESCRIPTION

Certain embodiments are described below with reference to singular and plural terms in order to provide a user friendly description of the technology disclosed herein. These terms are used for convenience purposes only and are not intended to limit the methods and systems described herein.

In certain configurations described herein, the sorbent tubes are effective to analyze components in a fluid stream, e.g., gas stream or liquid stream, without pre-extraction, pre-loading steps or post extraction, e.g., such as those used in EPA protocols TO13 and TO15. For example, the materials in the sorbent tubes described herein can be selected to permit direct loading of C6 to C44 species (or C4 to C44 species) on the sorbent tubes without liquid extraction or pre-loading of the components. In some instances, gas phase components can be drawn into the sorbent tubes using a pump or other suitable pressure device. In some configurations, the sorbent tube may comprise at least one material effective to provide a condensation surface without substantial absorbance to the material, e.g., glass beads. While not wishing to be bound by any particular theory, the glass beads may be effective to permit condensation of C22 to C40 (or above C40) species at the front end of the sorbent tube. Lower weight species, e.g., less than C22, can travel further into the sorbent tube and be adsorbed by one or more sorbent materials packed in the tube. Illustration of various fluid streams that comprise C6 to C44 species (or C4 to C44 species) and their analysis using the sorbent tubes described herein is discussed in more detail below. In some examples, the sorbent tube can be used to analyze components, e.g., C4 to C44 or C6 to C44 components, according to EPA protocol TO17.

In certain examples, residue in liquefied petroleum gas (LPG) is a contaminant that can lead to operational problems in some end use applications. The term "residue" as used herein generally refers to soluble contaminants in LPG within the C6 to C40 range. Typically, the residue materials have boiling points from 69° C. to 522° C. The LPG present tends to be primarily n-propane and may also include some species with 2 carbon atoms, 4 carbon atoms and 5 carbon atoms. Engines, micro-turbines, fuel cells and other equipment may be sensitive to residue levels as low as 10 mg/kg. Contamination of LPG can occur during production, transport, delivery, storage and use. A qualitative indication of the contaminants can help track down the source of the contamination from manufacture, through the distribution system, and to the end user. The systems and methods described herein can provide a lower detection limit, wider dynamic range, and better accuracy than gravimetric methods, e.g., ASTM D2158. If desired, the systems and methods described herein may provide desirable attributes including, but not limited to, improved detection limits, e.g., as low as 2 micrograms/gram, enhanced recoveries of the lower boiling components and greater dynamic range. Certain configurations of the systems and methods described herein may provide the amount of each particular residue material, e.g., the amount of each C6-C44 material present, or the total residue amount present.

In certain embodiments, the systems and methods described herein may be used to determine the residue in a liquefied petroleum gas stream using a sorbent tube and thermal desorption. For example, a liquefied petroleum gas stream comprising residue may be provided to a sorbent tube comprising sorbent materials. The sorbent materials can be selected such that the liquefied petroleum gas passes through the sorbent tube without any substantial adsorption, and the residue components become adsorbed to the sorbent materials. The adsorbed components may be thermally desorbed, e.g., using heat, gas flows, etc., to analyze the residue in the liquefied petroleum gas stream. Various examples of sorbent tubes effective to adsorb residue components while permitting passage of substantially all LPG are described herein.

In certain examples, a cross-section of a sorbent tube is shown in FIG. 1. The tube 100 comprises a body 110 which is typically a hollow body to permit packing of sorbent material within the hollow body. The body 110 of the tube 100 may comprise one or more metals, one or more glasses, one or more ceramics or combinations thereof. For example, the body 110 may comprise quartz, stainless steel, coated stainless steel or other metal or non-metal based materials that can tolerate the temperature cycles used to desorb the residue can be used. As discussed herein, it may be desirable to thermally couple the body 110 to a heat source for desorption of the adsorbed components. The tube 100 also comprises an inlet 120 and an outlet 125. Two different sorbent materials 130 and 140 are shown as being present within the body 110. The sorbent materials 130, 140 can be disposed within the hollow body 110 and occupy at least some portion of the internal volume of the body 110. In certain instances, the entire internal volume can be occupied by the different sorbent materials 130, 140, whereas in other examples, at least some portion of the internal volume can remain open, e.g., areas adjacent to the inlet 120 and the outlet 125 may be empty. In certain embodiments, a liquefied petroleum gas stream can be provided through the inlet 120 of the tube 100 such that certain species in the stream can adsorb, at least temporarily, to the sorbent materials 130, 140 in the sorbent tube 100. The sorbent tube 100 can be fluidically coupled to an analytical device, e.g., a GC or GC/MS, and a carrier gas can be swept through the sorbent device 100 in the general direction from the outlet 125 to the inlet 120, typically accompanied by heating, to desorb the adsorbed residue species. In particular, the carrier gas may be provided in a direction which is generally a counter-flow or antiparallel flow to the direction of flow of the liquefied petroleum gas stream into the sorbent tube 100. The adsorbed species exit the sorbent tube 100 through the inlet 120. The desorbed species may then be provided to a chromatography column (not shown) to separate them, followed by subsequent analysis using a suitable detector such as a flame ionization detector, mass spectrometer or other suitable detectors commonly found in or used with gas chromatography systems. If desired, the total amount of residue may be determined or the particular amount of one or more residue components can be determined, e.g., by using conventional standard curve techniques and standards. While not shown in FIG. 1, the tube 100 may comprise a selected amount of a material that is effective to provide a condensation surface without substantial absorbance to the material. In some instances, this material can be positioned upstream of the sorbent material 130, e.g., closer to the inlet 120 than the sorbent material 130. In some instances, the bed length, e.g., length along the longitudinal axis of the sorbent tube 100, of the various materials used in the sorbent tube 100 may be the same, whereas in other instances the bed length can be different.

In certain embodiments, the sorbent tubes used in the systems and methods described herein can include two, three, four, five or more sorbent materials. In some embodiments, two or more of the sorbent materials may be different, whereas in other embodiments two or more of the sorbent materials may be the same. The exact material used in the sorbent tubes can vary depending on the sampling conditions, desorption conditions, etc. In some examples, the sorbent tube can include a material comprising glass beads, glass wool, glass particles or combinations thereof or glass beads by themselves in combination with one or more other materials. While glass beads generally do not adsorb any of the materials, the glass beads can provide a high surface area to permit condensation of high molecular weight species, e.g., C22 and above, at the front end of the tube. The glass beads effectively remove the higher molecular weight species at the front end and permit the lower molecular weight species to travel down the tube and be adsorbed by one of the sorbent materials packed in the tube. In certain instances, two or more different types of glass beads can be present. In some embodiments, it may not be necessary to include a packed material to retain higher molecular weight components, e.g., C22 and above. As such, the sorbent tube may include internal surface features with high surface areas, e.g., integral glass beads, caps, chevrons, fins, glass beads etc. to retain the higher molecular weight components in the sorbent tube.

In some examples, one or more of the sorbent materials can be a graphitized carbon black such as, for example, Carbotrap™ B sorbent or Carbopack™ B sorbent, Carbotrap™ Z sorbent or Carbopack™ Z sorbent, Carbotrap™ C sorbent or Carbopack™ C sorbent, Carbotrap™ X sorbent or Carbopack™ X sorbent, Carbotrap™ Y sorbent or Carbopack™ Y sorbent, Carbotrap™ F sorbent or Carbopack™ F sorbent, any one or more of which may be used in its commercial form (available commercially from Supelco or Sigma-Aldrich) or may be graphitized according to known protocols. In other examples, the sorbent material can be carbon molecular sieves such as Carboxen™ 1000 sorbent, Carboxen™ 1003 sorbent, or Carboxen™-1016 sorbent, any one or more of which may be used in its commercial form (available commercially from Supelco or Sigma-Aldrich) or may be optimized according to known protocols.

In certain embodiments where three different materials are present, at least two of the materials may be one of the sorbent materials listed herein with each of the sorbent materials being a different sorbent material than the other sorbent materials used in the sorbent device. In such instances, two different sorbent materials would be present in the sorbent tube optionally with glass beads or other structure or material to provide an internal condensation surface. In some embodiments where three different sorbent materials are present, each of the sorbent materials may be one of the sorbent materials listed herein with each of the sorbent materials being a different sorbent material than the other sorbent materials used in the sorbent device. In such instances, three different sorbent materials would be present in the sorbent tube optionally with glass beads or other structure or material to provide an internal condensation surface. In some examples, the sorbent tubes described herein can include glass beads (or a material comprising glass beads) adjacent to the sorbent tube inlet and one or more materials other than glass beads downstream from the glass beads. For example, the sorbent tube may include glass beads and one or more Carbopack™ or Carbotrap™ materials. In some embodiments, the sorbent tube can include glass beads adjacent to the inlet and at least two different Carbopack™ materials downstream from the glass beads, e.g., closer to the outlet of the tube. In other embodiments, the sorbent tube can include glass beads adjacent to the inlet and at least two different Carbotrap™ materials downstream from the glass beads. In other embodiments, the sorbent tube can include glass beads adjacent to the inlet and at least one Carbotrap™ material downstream from the glass beads and at least one Carbopack™ material downstream from the glass beads. In packing the various materials, the material with the strongest adsorption strength is typically packed closest to the outlet and the sorbent with the weakest adsorption strength is packed closest to the inlet of the sorbent tube. As noted herein, the bed length of the various materials may be the same or may be different.

In certain examples, the mesh size or range of the materials in the sorbent tube can vary depending on the particular material selected. In some examples, the mesh size can range from 20 to about 100, more particularly from about 20-80, 30-70 or 40-60. In other examples, the mesh size range may be from about 20-40, 40-60, 60-80 or 80-100 depending on the material used in the sorbent tubes. Other suitable mesh sizes will be readily selected by the person of ordinary skill in the art, given the benefit of this disclosure.

In certain embodiments, the sorbent tubes described herein can be produced by disposing a suitable type and amount of sorbent material in a body. For example, one end of a hollow stainless steel tube or hollow glass tube can be equipped with a stationary screen to retain the first sorbent material in the tube. A first sorbent material can be disposed in the tube. A second fluid permeable bather can be placed on or in the disposed first sorbent material, and a second sorbent material can then be disposed on the second fluid permeable barrier. This process can be repeated until a desired number of sorbent materials are present in the tube. Following the last sorbent, a fluid permeable barrier can be placed against it and a clip can be inserted to hold the adsorbents in place. In this configuration, the sorbent materials are held in place on one end by a stationary fluid permeable barrier and on the other end by a clip. Other similar retention devices can be used to hold the sorbents in the body of the sorbent tube.

In certain examples, once the sorbent tubes are prepared, the integrity of the device can be assessed prior to use. For example, internal voids may form that can affect the quality of the tubes. In some examples, the quality of the sorbent tubes can be assessed as described in commonly assigned issued patent bearing U.S. Pat. No. 7,422,625, the entire disclosure of which is incorporated herein by reference, to ensure there are no undesirable voids or features in the sorbent device.

In certain embodiments, the sorbent tubes described herein can be used with an automated thermal desorption (ATD) gas chromatography system. In one embodiment, ATD works by heating the sorbent tube for a required amount of time to release compounds whose boiling point range from C4 to C44 species quantitatively from the sorbent material. During this heating, a carrier gas such as helium, nitrogen or hydrogen flows through the tube at a desired flow rate to transfer the contents of the sorbent tube onto a cooled secondary trap via a carrier gas, which is typically helium or hydrogen. This trap, which may contain, for example, glass beads and sorbent material similar to the sorbent tube, is then rapidly heated to desorb the collected components in a narrow band into the GC column for separation. A mass spectrometer or a flame ionization detector are common detectors used to provide the analysis, though other detectors such as, for example, thermal conductivity detectors, thermionic detectors, electron-capture detectors, atomic emission detectors, flame photometric detectors, photoionization detectors and other detectors may be used in any of the systems described herein. The information is sent to a computer containing an application which sends information to the instrument for control and collects information from the detector for analysis. This application has the ability to process this information which can provide quantitative and qualitative results. By including many different types of sorbent materials in the sorbent devices, a single desorption cycle can be used to desorb substantially all adsorbed species. Such desorption typically permits reuse of the sorbent device without further temperature treatment, e.g., baking for extended periods, to remove high molecular weight species. As described herein, the thermal desorption analysis may be performed by a separate system from that of the sampling system or the sampling system/thermal desorption analysis may be part of an integral system that can sample fluid streams and analyze them without removal of the sorbent tube from the system.

In certain embodiments, the sorbent tubes described herein may include one or more integral expansion chambers to permit vaporization of the fluid stream within the sorbent tube. For example, as described in more detail below, as a liquid stream is provided into the sorbent tube, a decrease in pressure from increased volume may be used to permit vaporization of the liquid stream within the sorbent tube and subsequent adsorption of residue vapor on the sorbent materials. Referring to FIG. 2, a sorbent tube 200 comprising an expansion chamber 210 adjacent to an inlet 205 is shown. The expansion chamber 210 provides for a larger open space within the sorbent tube 210 to permit a phase change of the liquid stream into a gas stream. The exact size and dimensions of the expansion chamber may vary, and, in certain instances, the expansion chamber may occupy about 25%, 30%, 35%, 40%, 45% or 50% more of the internal volume of the sorbent tube 200. For illustration purposes, the expansion chamber 210 is shown as occupying about 50% of the volume of the sorbent tube 200 with sorbent materials 220, 230 and 240 occupying the remainder of the volume of the sorbent tube 200 toward the outlet 207. Without wishing to be bound by any scientific theory, as liquid streams comprising liquefied petroleum gas vaporize, heat is absorbed from the surrounding portions of the tube which can result in cooling of the tube and potential formation of ice on the outside of the tube. Where an expansion chamber is present, the level of freezing of the tube can be reduced. While the tube may or may not form frost on an outer surface, generally the tube may be cold to the touch when the phase change from liquid to gas is occurring within the tube. In some instances, it may be desirable to size the expansion chamber so that some freezing does occur to permit visual observation that a phase change is occurring within the sorbent tube. In other instances, the sorbent tubes described herein can be used with a temperature sensor to determine if vaporization within the tube is occurring. The temperature sensor may be within the sorbent tube or may be thermally coupled to an outer surface of the sorbent tube.

In certain embodiments, the internal expansion chamber may comprise fins or other internal surface features that increase the overall internal surface area of the expansion chamber. Where fins or internal features are present, it may be desirable to omit one or more of the packing materials, e.g., the glass beads may be omitted, and the internal surfaces of the expansion chamber can be used to retain higher molecular weight species. For example and referring to FIG. 3, a sorbent tube 300 is shown that comprises an inlet 305 and an outlet 307, an expansion chamber 310, and two sorbent materials 330 and 340. The expansion chamber 310 comprises a plurality of fins 320 (or dividers) that can increase the overall surface area within the chamber 310. If desired, the overall length of the expansion chamber may be reduced where fins are present. The surfaces of the fins 320 may also be effective to receive higher molecular weight residue species, e.g., C22 and above, within the liquid stream, and retain those species within the tube 300. The sorbent materials 330, 340 may be the same or may be different, e.g., may be one or more graphitized carbon black materials.

In some embodiments, the expansion chamber can be inserted into the internal volume of the sorbent tube and sorbent materials may then be packed into the tube. In other instances, it may be desirable to couple an external expansion chamber to the sorbent tube to permit vaporization of the liquid stream in the external expansion chamber followed by vapor introduction into the sorbent tube from the expansion chamber. While some embodiments herein describe the presence of an integral or external expansion chamber, in some instances, the systems and methods can be used with a sorbent tube that does not include any expansion chamber.

Figure 4:
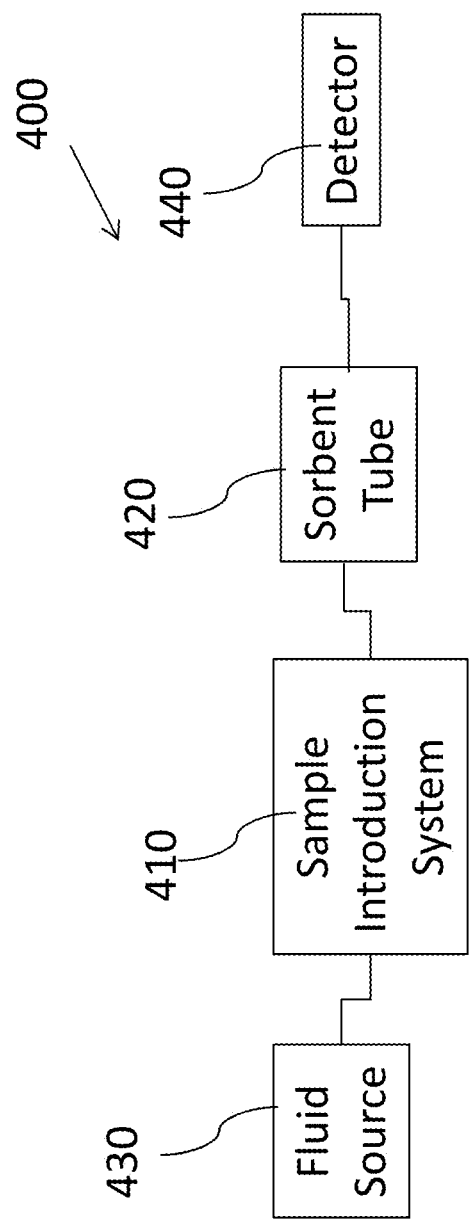
FIG. 4 is a block diagram of a system comprising a sorbent tube, in accordance with certain examples.

In certain examples, the sorbent tubes described herein can be used with a system that can provide a fixed volume (or a selected volume) of a liquid stream to the sorbent tube. For example, a block diagram of a sampling system is shown in FIG. 4. The sampling system 400 includes a sample introduction system 410 that is fluidically coupled to a sorbent tube 420. The system 410 can include suitable couplings to couple the system 410 to a fluid source 430, which may be, for example, a fluid source comprising LPG and any soluble residue. In some embodiments, the sorbent tube 420 may be fluidically coupled to a detector 440 by way of a chromatography column (not shown) to permit detection of species that become adsorbed to, or retained by, the sorbent tube 420. In other configurations, as described herein, the sorbent tube may be loaded using a system that does not include a detector, and after loading the sorbent tube may be removed from the sampling system and then placed into an instrument that can desorb the adsorbed components and analyze them.

Figure 5:
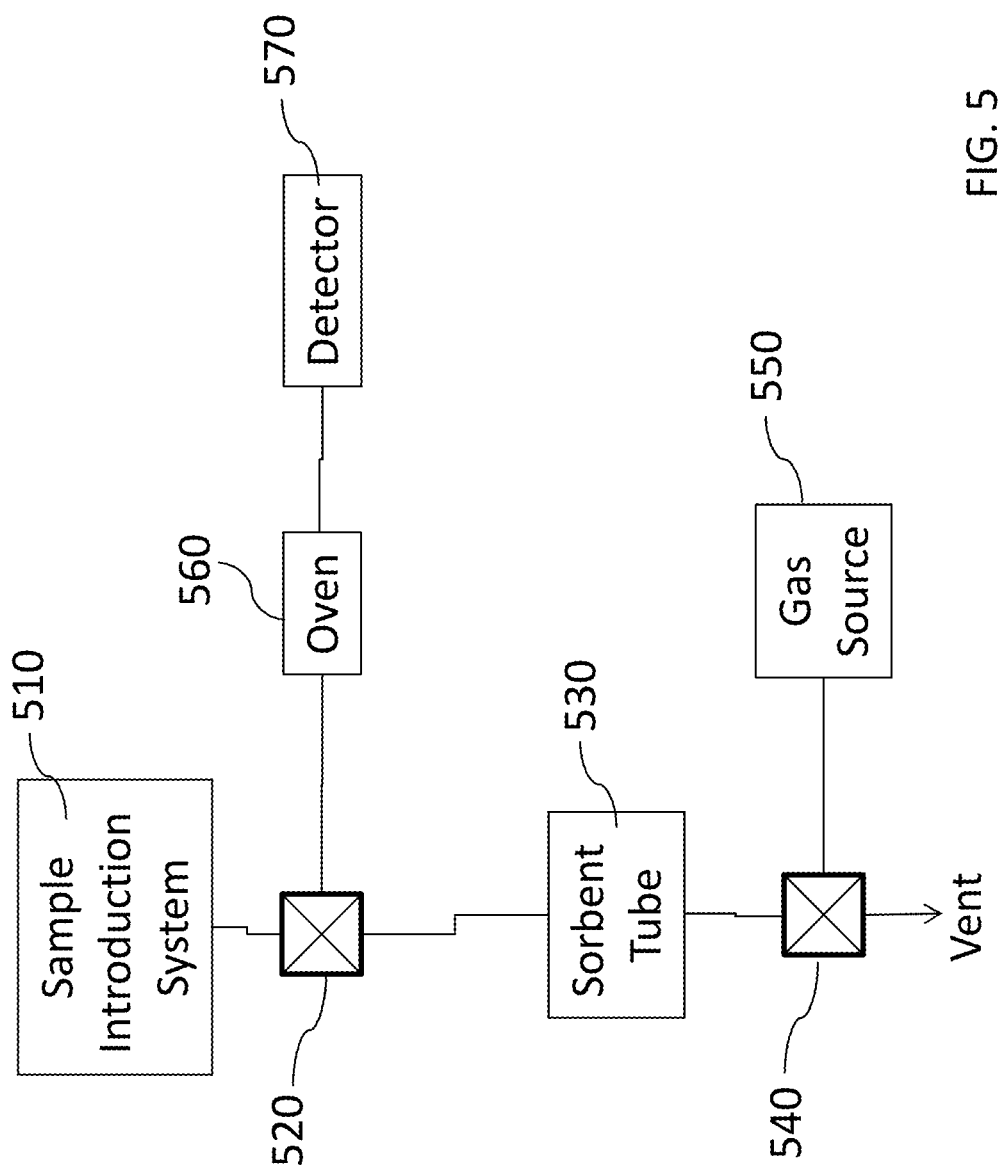
FIG. 5 is an illustration of a system comprising a system including a sorbent tube, in accordance with certain examples.

In certain examples, where it is desirable to leave the sorbent tube in place to analyze the adsorbed components, the sorbent tube may be fluidically coupled to an oven comprising a chromatography column through a 3-way valve. For example and referring to FIG. 5, in a first position of the 3-way valve 520, fluid may flow from the sample introduction system 510 to the sorbent tube 530 to load the sample onto the sorbent tube 530. The sample can be loaded onto the sorbent tube 530 in liquid form and may be permitted to expand and vaporize within the sorbent tube 530. The valve 520 may be actuated to a second position to fluidically couple the sorbent tube 530 and the column in the oven 560. A second valve 540 can be actuated to fluidically couple a gas source 550 to the sorbent tube 530 to carry desorbed species from the sorbent tube 530, as the sorbent tube 530 is being heated, to the column in the oven 560 for separation. As species elute from the column in the oven 560, they may be provided to the detector 570 for detection. In some instances, the sorbent tube can include an integral heater or jacket to assist in heating of the sorbent tube for desorption of the adsorbed species. For example, a temperature controlled jacket can be thermally coupled to the sorbent tube 530 to provide for temperature control. After the residue has been adsorbed to the sorbent materials and the LPG passes substantially through the sorbent tube without any substantial adsorption, the sorbent tube can be heated to desorb the adsorbed components. The gas flow from the carrier gas source 550 provides a flow from sorbent tube outlet to sorbent tube inlet, which is an opposite direction of flow from the flow used to introduce the sample into the sorbent tube 530. The system 500 may also include additional components between the sorbent tube and the oven including the column. For example, the system can include a condenser to liquefy the vaporized, desorbed components. Condensation of the components prior to entry to the chromatography column may be particularly useful to provide a narrow band of an analyte to the column to reduce diffusional broadening effects. The condenser may take many forms including liquid cooled jackets, Peltier coolers, pressurized chambers and other devices and systems that can convert a gas into a liquid by cooling or pressurization.

In certain embodiments, it may be desirable to spike or add standards to the sorbent tubes used herein to provide internal standards that can be used in the analysis. To add standards to the tube, the systems described herein can be used or the standards can be added directly to the tubes. For example, a syringe can be filled with an appropriate volume of standards. The needle may be inserted into the sorbent tube to inject the standards into the tube through the sampling inlet, e.g., adjacent to the weakest sorbent strength material. An air flow can be introduced into the tube to assist in introduction of the standards. For example, a conventional GC inlet can be coupled to the tubes to provide a gas stream into the tubes.

Figure 6B:
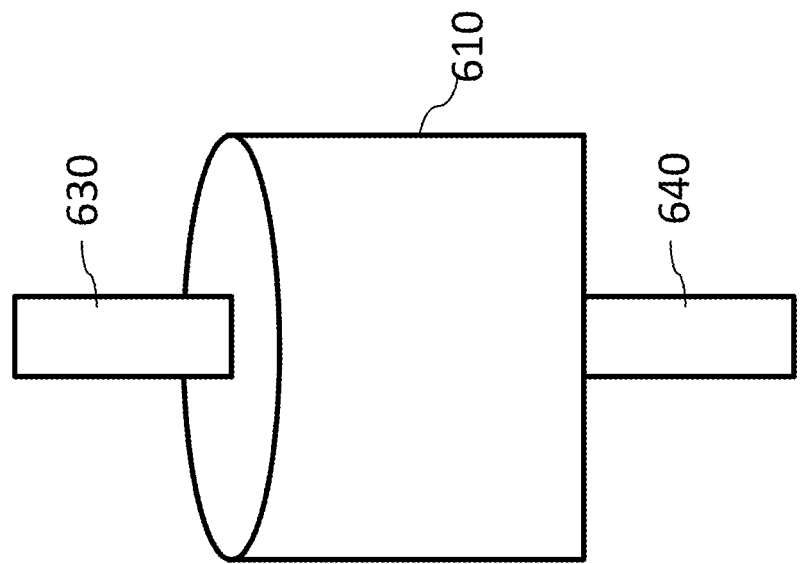
FIGS. 6A and 6B are illustrations of a filter configured as a canister, in accordance with certain examples.
Figure 6A:
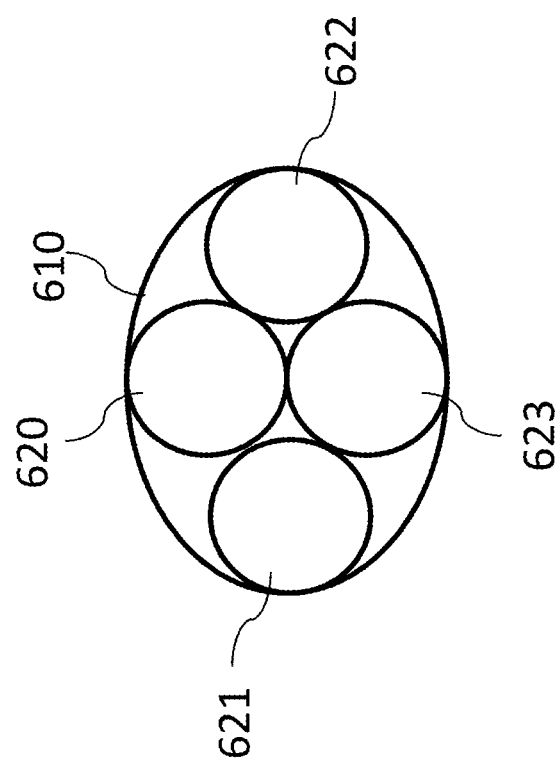

In certain embodiments, the sorbent tubes described herein can be used as a fuel filter, e.g., an in-line fuel filter, to remove residue from the fuel prior to the fuel being provided to an engine or burner The fuel filter may take many different forms including a single in-line fuel filter, a canister type fuel filter comprising a plurality of channels or other forms. The fuel filter typically includes at least one sorbent material as described herein, e.g., two or more sorbent materials or three or more sorbent materials or glass beads in combination with one, two, three or more sorbent materials. Referring to FIG. 6A, a top view of canister type fuel filter 610 is shown comprising a plurality of channels 620-623. A side view is shown in FIG. 6B. A fuel inlet line 630 is fluidically coupled to the fuel filter 620, and a fuel outlet line 60 is fluidically coupled to the fuel filter 620. As fuel enters into the fuel filter 610, the flow is split into each of the channels 620-623, each of which may include one or more sorbent materials effective to adsorb substantially all residue from the fuel stream and pass all liquefied petroleum gas in the fuel stream through the outlet 640. In some instances, the channels 620-623 may be configured to receive integral filters, e.g., ones comprising a body and sorbent materials that can drop into the channels and act as filters. In other embodiments, the sorbent materials may be packed directly into the channels 620-623. In some instances, the fuel filter 610 can be cleaned or flushed in a cleaning step by heating the fuel filter 610 and back flushing it with an inert gas to remove any adsorbed residue. In certain embodiments, the fuel filter may be effective to remove the residue from an LPG stream such that any residue exiting the fuel filter will be about 20 ppm or less, more particularly about 10 ppm or less, e.g., less than 9, 8, 7, 6, or 5 ppm. While the residue materials may include varying carbon atoms, it may be desirable to reduce or filter out residue material with large numbers of carbons, e.g., C21 or greater, to a higher degree than residue material with a lower level of carbons, e.g., C6 to C12. For example, the fuel filter may be constructed and arranged to provide a filtered stream that includes 35 ppm or less C6 to C12 residue materials, 20 ppm or less C13 to C20 residue materials and 10 ppm or less C21 to C44 materials. By filtering out the larger materials, reduced varnish buildup (or reduced buildup of other materials which can impair fuel flow) may occur, which can increase the overall lifetime of the component to which fuel is supplied.

In certain examples, the exact sorbent materials used in the in-line filters can vary depending on the device used with the filter. For example, certain engines or burners may be able to tolerate higher residue amounts, and filters with lower filtration capacity can be used to increase overall fuel flow. In some embodiments, the sorbent materials may comprise glass beads, Carbotrap® materials, Carbopack® materials or other suitable materials. If desired, the filter may also include an expansion chamber to permit vaporization of the liquid fuel within the filter. In some embodiments, the overall size and amount of materials present in the fuel filter may be substantially larger than what is present in a sorbent tube used for sample analysis. For example, depending on the fuel flow through the device, it may be desirable to size the body of the fuel filter to be several inches or feet in diameter such that the capacity of the filter is suitable for use with the fuel flow.

In some embodiments, the filters can be used with an engine such as an engine present in an automobile vehicle. Many commercial vehicles and heavy equipment can include liquefied petroleum gas engines. Similarly, many generators for backup power or primary power may use liquefied petroleum gas as a fuel source to provide energy. In such instances, the fuel filters described herein can be used to increase engine lifetime, reduce spark plug fouling or otherwise provide a smoother running engine. In other examples, the in-line filters can be used with a burner such as those commonly found on grills, cooktop stoves for recreational vehicles, in furnaces or in other devices which burn liquid propane to provide heat energy in some form.

In certain embodiments, the sorbent tubes described herein may also be used to analyze BTEX (benzene, toluene, ethyl benzene and xylenes) in combination with PAHs (polynuclear aromatic hydrocarbons), e.g., the EPA regulated PAHs which include, for example, naphthalene, methylnaphthalene, 1-methylnaphthalene, acenaphthene, acenaphthylene, anthracene, benzo[a]anthracene, benzo[a] pyrene, benzo[e]pyrene, benzo[b]fluoranthene, benzo[ghi] perylene, benzo[j]fluoranthene, benzo[k]fluoranthene, chrysene, coronene, dibenzo(a,h)anthracene, fluoranthene, fluorene, indeno(1,2,3-cd)pyrene, phenanthrene and pyrene. It is a substantial attribute that a single analysis can be performed using the sorbent tubes described herein to simultaneously analyze both BTEX and PAHs in an air stream as conventional analysis, e.g., EPA TO13 or TO15 protocols, employs two different and separate analyses. In some embodiments, the sorbent tubes effective to analyze air for BTEX and PAHs may include one, two, three or more sorbent materials, optionally in combination with glass beads, as described in reference to the other sorbent tubes described herein. In certain instances, BTEX and PAHs may be outgassed in various scenarios, e.g., coal mines, Superfund clean-up sites or other areas where the earth or soil may be moved or otherwise disturbed. To ensure the workers and/or local population are not inhaling high levels of BTEX and/or PAHs, the sorbent tubes described herein can be used sample the ambient air at a desired site. Passive sampling, e.g., sampling without the use of a pump to introduce an air flow into the sorbet tube can be used, or active sampling can be used, e.g., where a pump is used to provide an air flow into an inlet of the sorbent tube. In some instances, ambient air may be monitored continuously or periodically to determine how much BTEX and/or PAHs are present.

In certain embodiments, BTEX and PAHs can be sampled by introducing a fluid stream, e.g., an air stream, into a sorbent tube effective to reversibly adsorb potential BTEX and PAHs toxic contaminants that are present in the fluid stream, desorbing the adsorbed BTEX and PAHs from the sorbent tube, and detecting the BTEX and PAHs. It is a substantial attribute that the components in the air stream can be introduced directly onto the sorbent tube to permit analysis of C6 to C44 (or C4 to C44) components without pre-extraction, pre-capture or liquid extraction steps. For example, the EPA Method TO13 protocol uses filters and sorbent cartridges to load sample. Solvent extraction is then performed on the filters and sorbent cartridges. The solvent extracts are then concentrated, filtered and analyzed by GC-MS. In the EPA Method TO15 protocol, an air sample is first introduced into a stainless steel canister. The air in the canister must then be introduced into a multisorbent concentrator to remove the water. After concentration and drying, the materials may then be analyzed. The sorbent tubes described herein permit analysis of all components possible, in the C4 to C44 boiling point range, using the TO15 and/or TO13 protocols, but permit omission of the onerous sample capturing steps and extraction steps used in those protocols. The direct sampling, e.g., without liquid extraction or concentrating steps, permit the tubes to be placed in the ambient environment and used to directly sample various PAH species in the ambient environment, e.g., using EPA Method TO17 in a single analysis in place of having to use both methods TO15 and TO13. One analysis instead of two saves time, reduces cost, and reduces solvent emission into the atmosphere making it more environmentally friendly. Other attributes of using the tubes described herein is reduced weight, sample tubes are less expensive to ship, take up less space for shipping, have a smaller form factor and are easier to handle, permit the analysis of polar and non-polar species, and permits recovery of analytes with a boiling point greater than naphthalene, as naphthalene is a struggle to recover out of a canisters.

In certain embodiments, the method further comprises desorbing the adsorbed components from the sorbent tube by heating the sorbent tube. In other embodiments, the method comprises desorbing the adsorbed components from the sorbent tube by heating and providing a carrier gas to the sorbent tube. In additional embodiments, the method comprises separating the vaporized components using chromatography, e.g., with or without first condensing the desorbed components prior to introduction to a chromatography column. In further examples, the method comprises sequentially detecting each of the separated, desorbed components to determine the amount of BTEX and PAHs in the liquid stream. In some instances, a single desorption cycle can be used to desorb substantially all adsorbed BTEX and PAH species from the sorbent tube, e.g., a single cycle of heating using a carrier gas. Such desorption typically permits reuse of the sorbent device without further temperature treatment, e.g., baking for extended periods, to remove high molecular weight species.

In some instances, the sorbent devices described herein that are configured for analysis of BTEX and PAHs can be used to continuously monitor the air quality in an air space occupied by animals such as humans. The reusability of the sorbent devices permits automated monitoring without having to change out the tube. For example, air may be periodically sampled in a coal mine, near railroad operations or other shipping operations, near power plants, or the like for the presence of BTEX and/or PAHs that may lead to adverse health effects. In such instances, a single sorbent device can be used repeatedly. The ability to reuse the same tube without having to subject the tube to high temperatures after analysis permits their use in these applications and others including, but not limited to, repetitive air space sampling underground, e.g., in coal mines, or above ground in scenarios where it may not be feasible to heat the tubes for extended periods prior to reuse. Further, the ability to capture and analyze PAHs without liquid solvent extraction from the sorbent tube simplifies the overall analysis of the PAHs and is an environmentally friendly analysis.

In other instances, a sorbent tube effective to retain BTEX and PAHs present in a liquid stream, e.g., air, the sorbent tube comprising a body comprising an inlet and an outlet, and an effective amount of each of a plurality of sorbent materials disposed within the body, the plurality of sorbent materials together effective to reversibly adsorb substantially all BTEX and PAHs in the fluid stream, e.g., air at ambient temperature and pressure. In certain examples, the sorbent tube may comprise at least three different materials. In other examples, at least one of the three sorbent materials comprises glass beads. In some examples, one of the three different materials is effective to provide a condensation surface without substantial absorbance to the material, e.g., comprises glass beads. In other examples, one of the three different materials is glass beads and the other two materials are different graphitized carbon black sorbent materials. In further examples, the glass beads and sorbent materials are effective to reversibly adsorb substantially all the BTEX and PAHs with six or more carbon atoms.

In other examples, the sorbent tube can include a temperature jacket thermally coupled to the body of the sorbent tube. In additional embodiments, the sorbent tube can include at least two or three different sorbent materials, in which the sorbent materials are packed from a weakest sorbent strength adjacent to the inlet and a strongest sorbent strength adjacent to an outlet. In some examples, at least one of the three different materials comprises glass beads. In some embodiments, one of the three different sorbent materials is glass beads. In other examples, one of the three different materials is glass beads and the other two sorbent materials are different graphitized carbon black sorbent materials. In further embodiments, at least three different materials, in which the sorbent materials are packed between the inlet and an outlet of the body can be used to sample BTEX and/or PAHs.

In certain examples, a system comprises a sampling pump fluidically coupled to the sorbent tube such that the flow of ambient air moves through the tube from weak to strong adsorbent, e.g., from inlet to outlet of the sorbent tube, to permit the BTEX and PAHs (or analytes within the C4 to C44 boiling point range) to reversibly adsorb to the adsorbent. The exact flow rate used to permit adsorption may vary and where passive sampling is used, e.g., the pump is omitted, air currents provided from atmospheric wind may be sufficient to permit sampling. In other instances, an active pump may be fluidically coupled to the surrounding environment and may draw in ambient air and pump it into the sorbent tube. The sample introduction device, e.g., a pump, can be configured to provide the fluid stream to the plurality of sorbent materials to reversibly adsorb substantially all BTEX and PAHs in the fluid stream. In a typical configuration, a fluid line is used to fluidically couple the pump to an inlet of the sorbent tube. If desired, one or more filters or pre-filters may be present to remove certain species, e.g., particulate matter or other solid materials suspended in the air stream, from the air stream prior to it being provided to the sorbent tube. In certain instances, the pump may draw the fluid sample directly onto the materials of the sorbent tube without any pre-concentration or liquid extraction steps.

While various sorbent tubes are described herein, it may be desirable to use a first type of sorbent tube for one sample and a different type of sorbent tube for a different sample. In some instances, standard curves may be produced by providing standard to glass sorbent tubes, whereas LPG residue or BTEX/PAH samples may be added to metal sorbent tubes. In addition, the inner diameter of the inlet of the sorbent tube may be the same or different than the inner diameter of the outlet of the sorbent tube. In some examples, it may be desirable to reduce the inner diameter of the outlet to assist in reducing analyte dispersion and band broadening.

Certain specific examples are described below to illustrate further some of the novel aspects and embodiments described herein.

Example 1

Liquefied Petroleum Gas (LPG) can be sampled by ASMT D1265 or ASMT D3700. A single phase sample of LPG can be introduced into a sorbent tube. The sample is maintained at a pressure above its bubble point as it is released directly onto the hydrocarbon-selective absorbent tube material, thereby trapping the C6 plus hydrocarbons (residue). Almost all of the C5 minus components pass through the sorbent material(s). The loop weight containing the sample provides the sample mass. The sorbent tube is placed onto the thermal desorber, which desorbs the residue from the tube directly onto the analytical column of the gas chromatograph for separation, detection and quantitation. The data handling system acquires the raw data from a flame ionization detector. The processing method, which contains the response factor (RF) and integration parameters from standards previously analyzed, is applied to the sample, and the mass of residue in the sample is calculated. While the exact temperatures and flow rates may vary, Tables 1 and 2 provide some illustrative parameters.

TABLE 1

Thermal Desorber Parameters

| | |
|---|---|
| Sorbent Tube | Desorb for 18 min @ 375° C. @ 30 mL/min |
| Concentrator Trap | Trap Low 5° C.; Trap high 380° C.; Trap Hold |
| Pneumatics | Inlet split 50 mL/min; Outlet split 30 mL/min; analytical column flow 0.8 mL/min |

TABLE 1-continued

Thermal Desorber Parameters

| | |
|---|---|
| Ambient Purge* | Purge for 3 min @ ambient temp @ 50 mL/min |
| Transfer Line** | 290° C. |
| Valve Temp** | 260° C. |
| GC Cycle Time | 34 min |

TABLE 2

Gas Chromatographic Parameters

| | |
|---|---|
| Oven | 35° C. for 4 min, ramp 15° C./min to 230°; ramp 10° C./min to 330° C. and hold for 3 min |
| GC Run Time | 30 min |
| Detector temp | 340° C. |
| Detector Flows** | 40 mL/min Hydrogen; 400 mL/min Air |

*A purge is used to rid the tube of residual oxygen and $C_5$ minus prior to primary desorption.

**Manufacturer specific parameter. Refer to manufacturer's guidelines for these parameters.

Example 2

Figure 7:
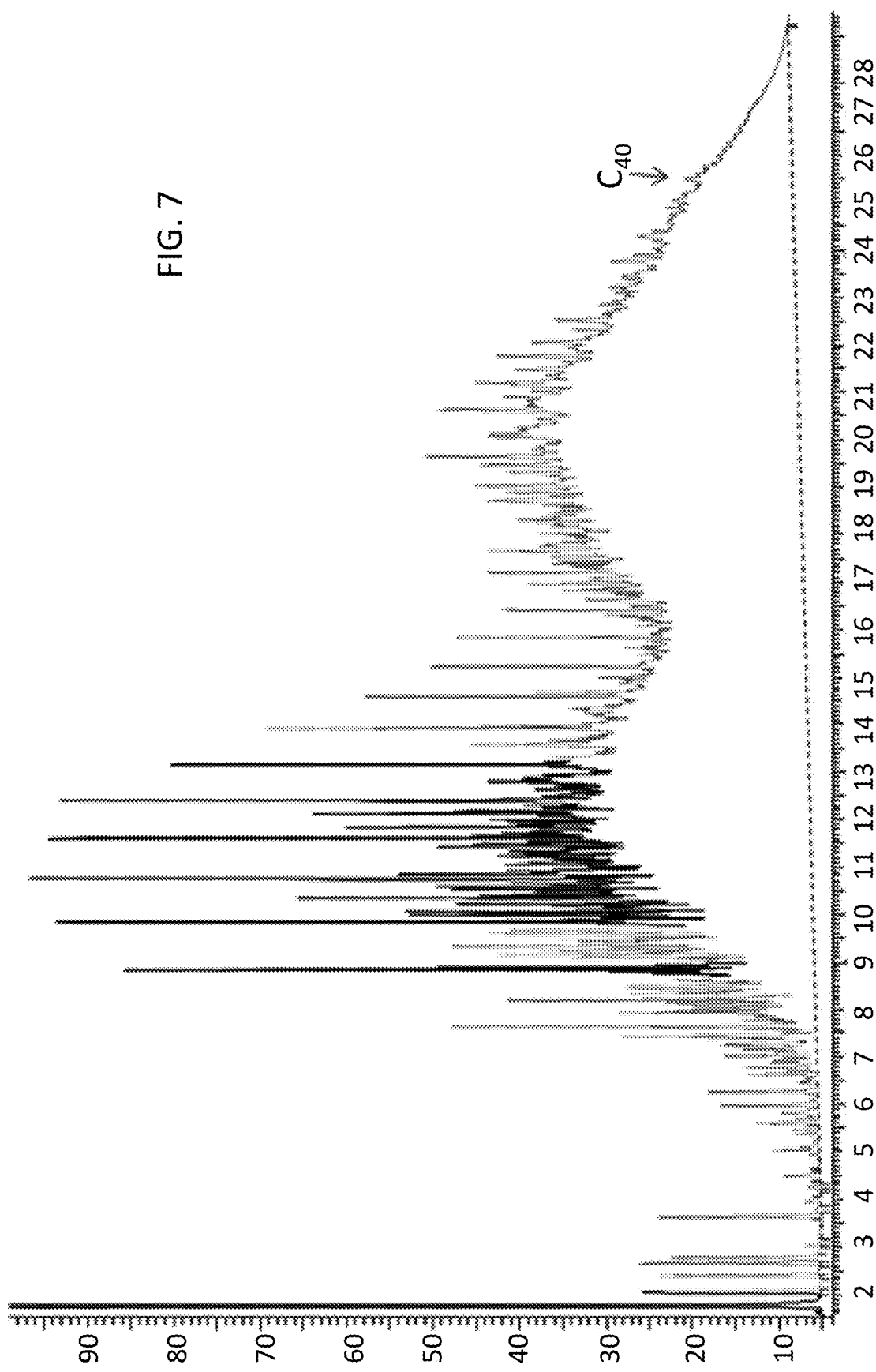
FIG. 7 is a graph showing signal response versus time for a series of standards, in accordance with certain examples.
Figure 8:
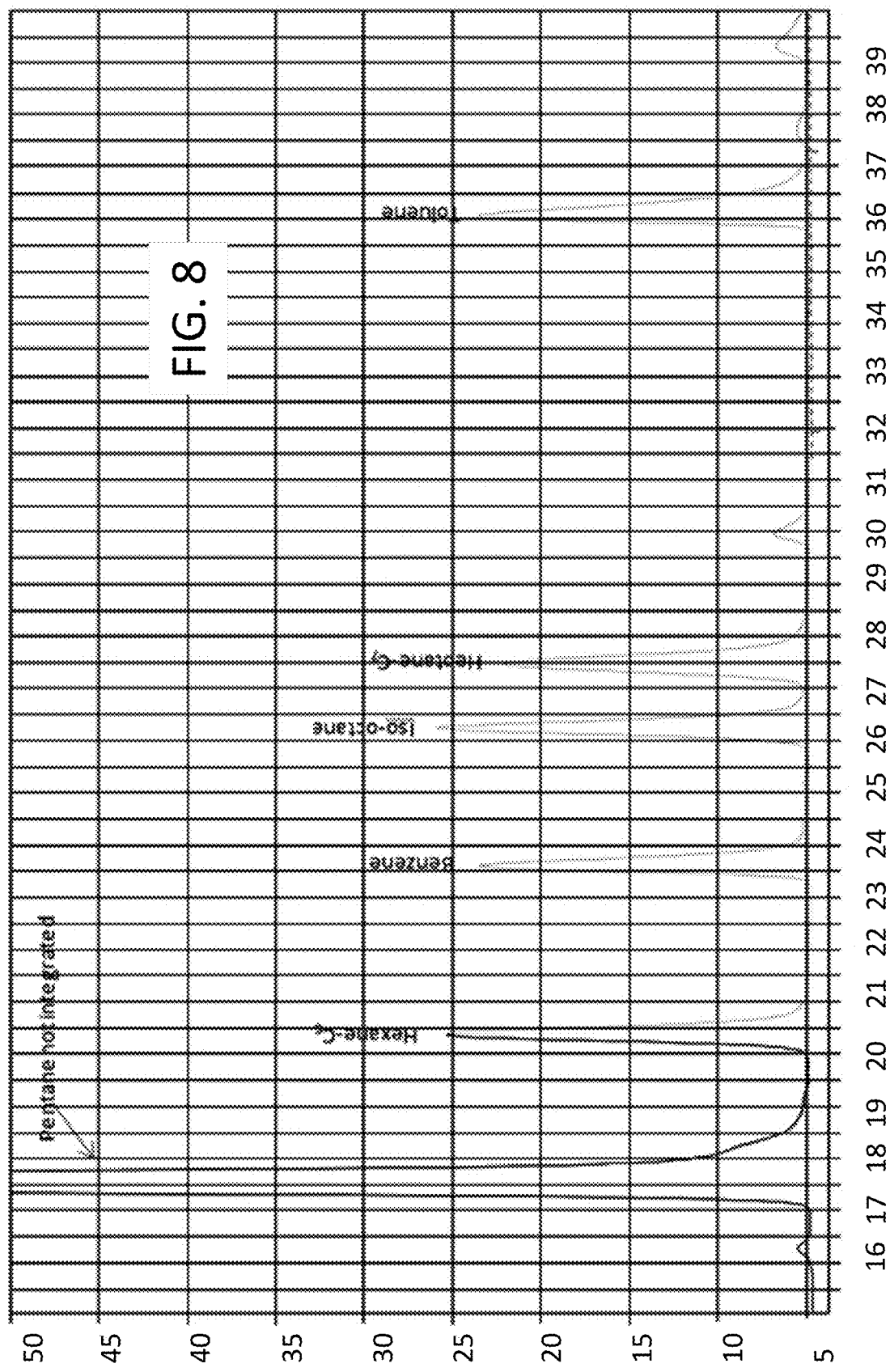
FIG. 8 is an expanded portion of the graph of FIG. 7, in accordance with certain examples.

The thermal desorption apparatus can be calibrated as described in this example. To cover the residue range, a component mixture (hexane, heptane, iso-octane, and toluene) is used for the lower boiling point region (gasoline); diesel is used for the mid-range and compressor oil is used for the higher boiling point region. Since speciation is usually not required, a sum of the entire residue area is used. The "timed group" start time for this sum is immediately following the elution of pentane and the end point for this sum is when the compressor oil returns to baseline (some compressor oil elutes past C40). FIG. 7 displays this integration noting the time points for the timed group for response (area) from the standard. FIG. 8 is an expansion of this chromatogram on the x axis demonstrating the separation of pentane (solvent) and hexane. A three or five level calibration is sufficient covering the range of sample concentration. For volatile stock standard, a 0.02 g/mL solution may be produced using pentane as a solvent. For standard #1, approximately 3.5 g of diesel and 4.0 g of compressor oil (recording the mass to 0.0001 g) can be added to a 10 mL volumetric flask. Add 600 uL of Volatile Stock (solution with pentane) by inserting stock directly into mixture, and then fill to mark with pentane. This standard contains 1.2 µg/µL volatiles and 750 µg/µL diesel plus compressor oil. The exact concentrations can be calculated based on recorded masses. For standard #2, a 10 mL volumetric flask can be filled about half full with pentane. Using a 1 mL gas tight syringe, transfer 1 mL of standard #1 into pentane and then fill to mark with pentane. This standard contains 0.12 ug/uL volatiles and 75 ug/uL diesel plus compressor oil. The exact concentrations can be calculated based on recorded masses from standard #1. For standard #3, a 5 mL volumetric flask can be filled about half full with pentane. Using a 0.25 mL gas tight syringe, transfer 0.20 mL of standard #2 into pentane and then fill to the mark with pentane. This standard contains 0.0048 µg/uL volatiles and 3.0 µg/uL diesel plus compressor oil. The exact concentrations can be calculated based on recorded masses from standard #1.

The following amounts of materials can be transferred into standard sorbent tubes. In this example, seven concentrations were prepared because of the broad range.

| 1 µL Stock # µg on tube | 6 µL Stock # µg on tube | 0.5 µL Stock µg on tube | 2 µL Stock # µg on tube | 5 µL Stock # µg on tube | 1 µL Stock # µg on tube | 2 µL Stock # µg on tube |
|---|---|---|---|---|---|---|
| 3. | 18.03 | 37.56 | 150.24 | 375.60 | 751.20 | 1502.40 |

Figure 9:
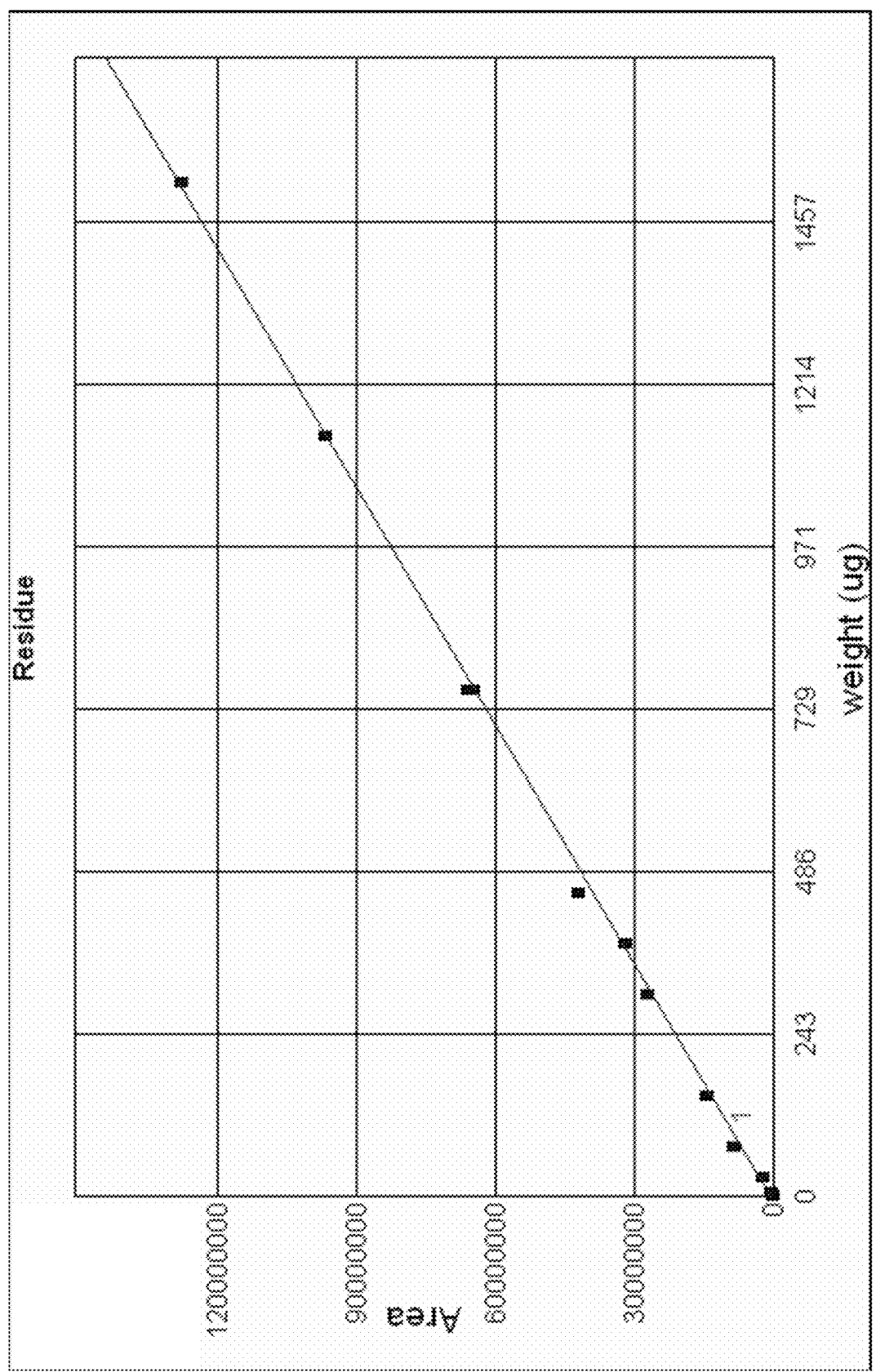
FIG. 9 is a standard curve, in accordance with certain examples.

The standard curve represents response vs. mass on tube, where the y axis is response of each standard (the time integration starting immediately after the elution of pentane through compressor oil), and the x axis is micrograms on the tube. FIG. 9 represents a first order plot containing 11 concentrations from 3 to 1517.4 µg with correlation coefficient ($R^2$) of 0.9990.

Figure 10:
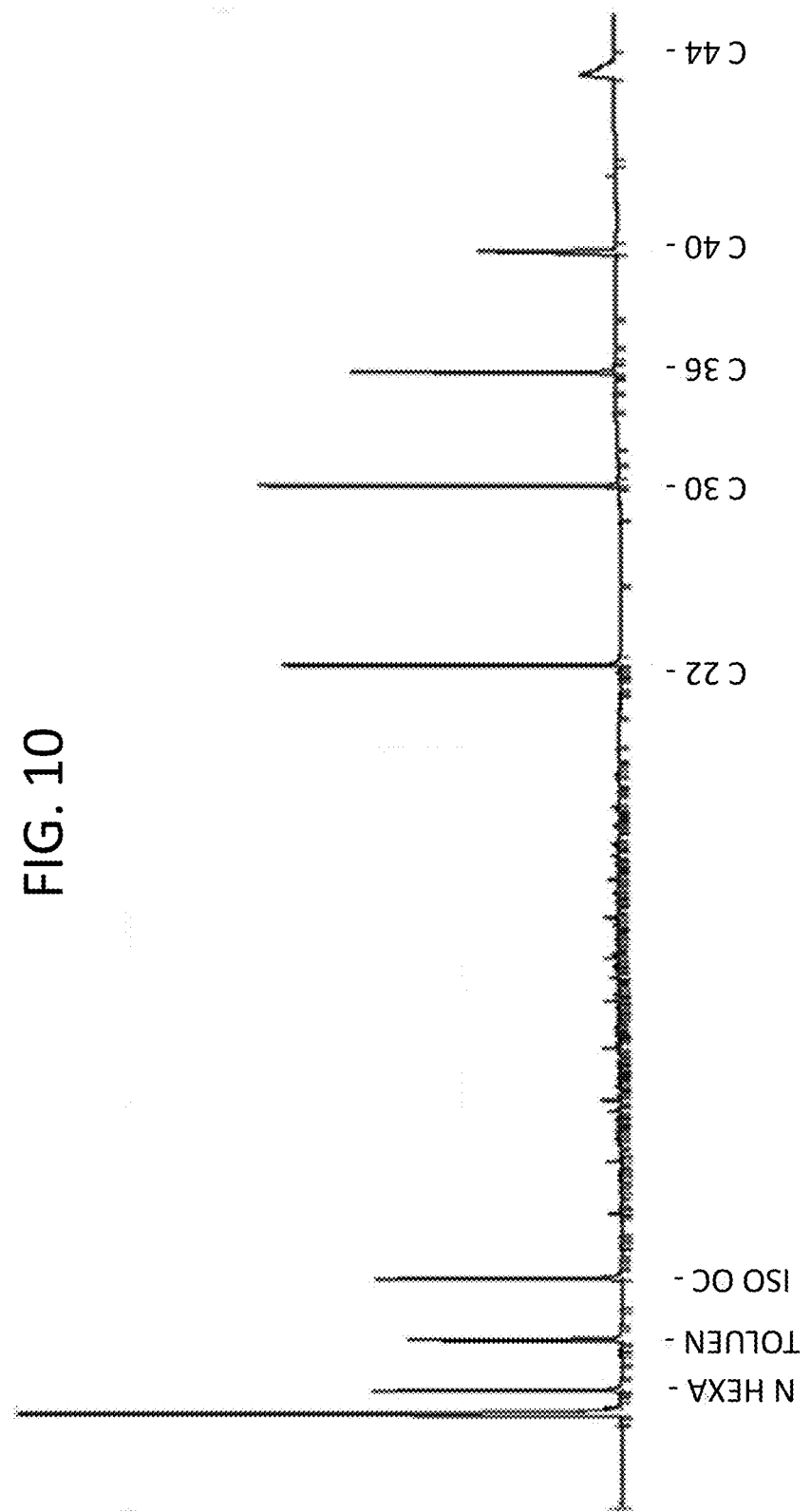
FIG. 10 is a chromatogram of a standard used to verify and confirm recovery from C6 to C40, in accordance with certain examples.

A standard covering the range from C6 to C40 at approximately 50 ppm each was injected to designate boiling point retention, to locate the time for integration and to ensure recovery of the analytical system. FIG. 10 represents a chromatogram of a standard used to verify and confirm recovery from C6 to C40 of the instrument by injecting this standard onto a standard tube. Table 3 documents the results from this standard confirming recovery for residue in this range and showing retention times (RT).

TABLE 3

| Compound | RT | % Recovered |
|---|---|---|
| n-hexane | 2.53 | 94.2 |
| Iso-octane | 3.64 | 99.5 |
| Toluene | 4.98 | 102.4 |
| C22 | 18.41 | 100.0 |
| C30 | 22.33 | 112.2 |
| C36 | 24.82 | 106.9 |
| C40 | 27.46 | 102.7 |

Example 3

An LPG sample may be analyzed as follows. An LPG sample can be obtained using ASTM D1265 or D3700, or collect a sample directly onto a sorbent tube from a sampling point on the LPG system. An instrument blank test can be performed to ensure the system is not contaminated, by analyzing an empty sorbent tube (a tube without adsorbents). The calibration can be performed with standards as described herein to calibrate the method for quantitation. The instrument parameters found in Tables 1 and 2 can be followed. Blank sample can be injected to ensure carryover has not occurred. The results should be non-detectable or below the limits of quantitation.

LPG can be loaded onto the sample tube as described herein. The sorbent tube with sample can be analyzed using method parameters described in Tables 1 and 2. Insert the sample mass as the divisor in the sequence so that the proper calculations are performed. The results can be calculated by the data handling system and results are reported. If the amount of residue in a sample exceeds the calibration range, dilution of the sample or a smaller volume with correction factor can be performed so that the sample falls within the calibration range. If a sample amount falls below the reporting limit, the sample amount should be reported as below the reporting limit.

Example 4

Figure 11:
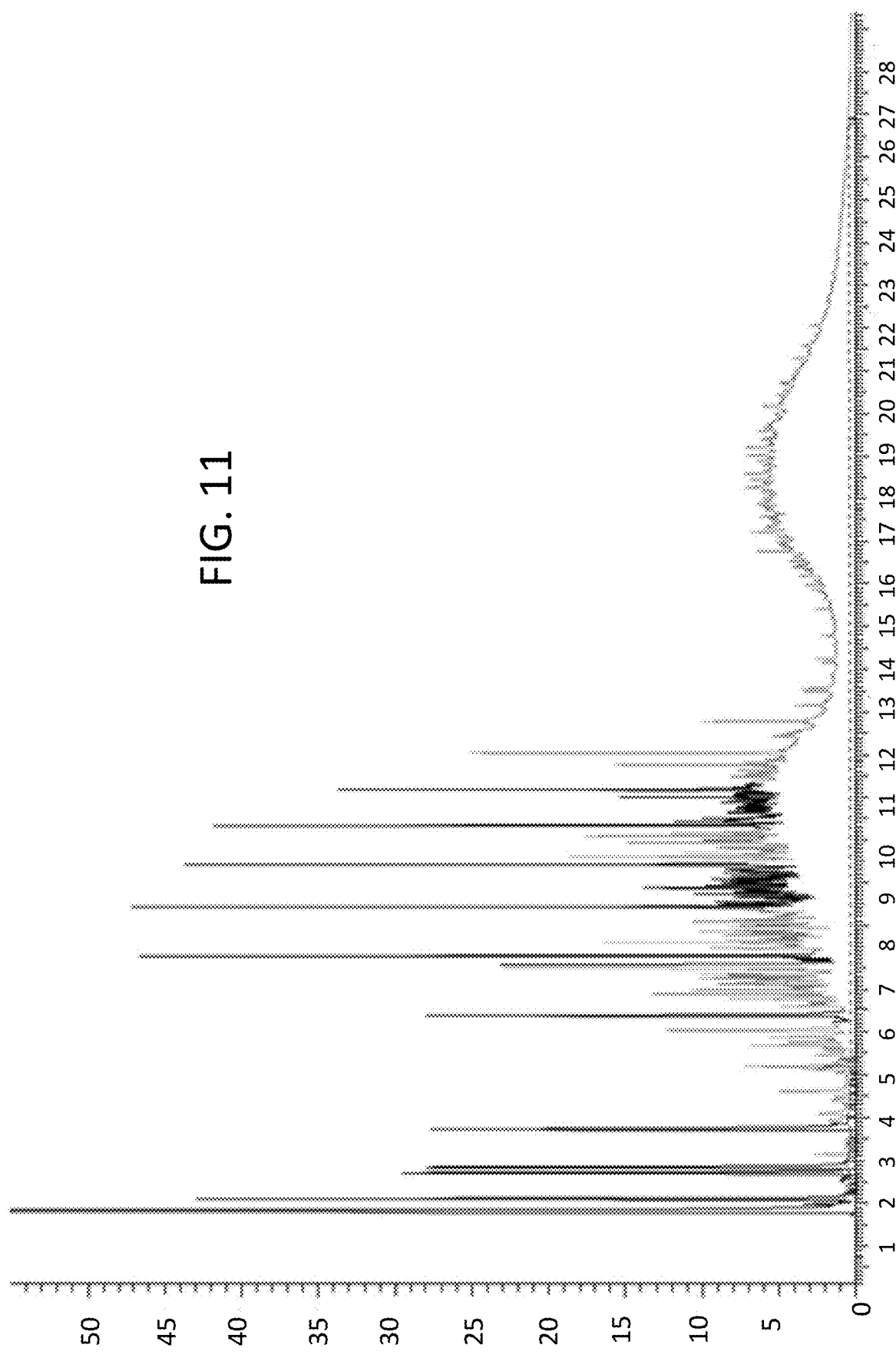
FIG. 11 is chromatogram showing clean LPG spiked with a residue standard, in accordance with certain examples.

FIG. 11 represents clean LPG spiked with a residue standard. The concentration of this standard was 7.9 µg/g (C6 through C8), 62.9 µg/g diesel and 69.3 ug/g compressor oil resulting in a total residue concentration in LPG of 139 µg/g. Sample mass on tube was 0.4269 g. Note that propane and butane in the LPG are not detected or retained by adsorbents, and therefore do not interfere with residue measurements. The standard concentration range is from 3 to 1500 µg. Since the sample amount being used is approximately 0.45 g, the method dynamic range is from 6.7 to 3300 µg/g.

Example 5

Figure 12:
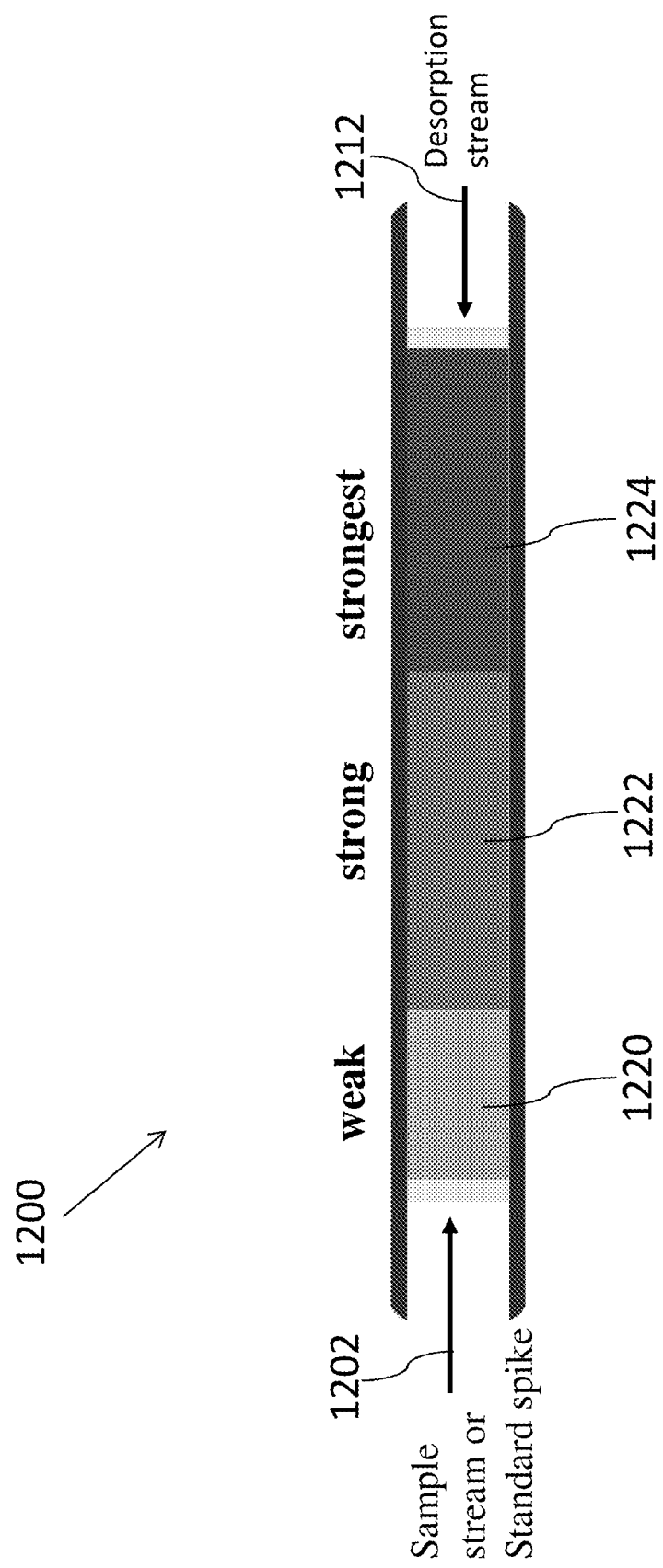
FIG. 12 is an illustration of a sorbent tube fluidically coupled to a condenser, in accordance with certain examples.

An illustration of a sorbent tube 1200 is shown in FIG. 12. A sample and/or standards are introduced into the sorbent tube 1200 in the direction of arrow 1202. Once the sample is adsorbed to the sorbent material, sample introduction may cease and a carrier gas may be provided to the sorbent tube in the direction of arrow 1212. The carrier gas, in combination with heating of the sorbent tube, if desired, results in desorption of adsorbed species from the sorbent tube 1200. The sorbent tube 1200 is shown as including three different materials 1220, 1222 and 1224. The materials are typically arranged (from inlet to outlet) in order of strength with the weaker sorbent materials being adjacent to the inlet and the strongest sorbent material being adjacent to the outlet. While the exact composition of the sorbent materials can vary depending on the intended use of the sorbent tube 1200, in some embodiments, the sorbent materials 1220 may be glass beads and the sorbent materials 1222, 1224 may be a Carbotrap® or a Carbopack® material. For example, where residue in LPG is analyzed, the sorbent material 1220 may be glass beads, the sorbent material 1222 may be Carbotrap® C and the sorbent material 1224 may be Carbotrap® B. Where the sorbent tube 1200 is used to analyze BTEX and PAH components, the sorbent material 1222 may be Carbotrap® C and the sorbent material 1224 may be Carbotrap® B or Carbotrap® X.

In some instances, the different sorbent materials 1220, 1222 and 1224 may be separated by a fluid permeable barrier, e.g., a fluid permeable mesh or fluid permeable metal screen. While FIG. 12, for illustration purposes, shows the materials 1222, 1224 being present at about the same length along the tube 1200, it may be desirable to include a particular sorbent material in a larger amount that the other sorbent materials. For example, where a sample is suspected of having a large concentration of a particular analyte, the sorbent material effective to adsorb and desorb that analyte may be present in a larger amount/volume to provide for increased loading of that analyte. In certain examples, the sorbent materials 1220, 1222 and 1224 can each be present at substantially the same weight ratio, e.g., 1:1. In other examples, the different sorbent materials can independently be present in weight ratios ranging (for any two sorbent materials) from 3:1, 2.5:1, 2:1, 1.5:1, 1.1:1, 0.9:1, 0.8:1, 0.7:1, 0.6:1, 0.5:1, 0.4:1, 0.3:1, 0.2:1, 0.1:1 or any ratio in between these illustrative ratios. It may be desirable to determine the relative weight ratios using the first sorbent material (the one closest to the sampling inlet) as the normalization factor, and the amount of each of the other sorbent materials that is present can be divided by the amount of the first sorbent material that is present to determine the relative weight ratios present in the sorbent device. In some examples where a three bed sorbent device is used, a ratio (based on weight of the sorbent material with the weight of the first sorbent material 1120 being used as a normalization factor) of about 1 of the first sorbent material 1220, 0.74 of the second sorbent material 1222, and about 0.58 of the third sorbent material 1224 may be present in the sorbent device 1200. Additional suitable amounts of the sorbent materials will be readily selected by the person of ordinary skill in the art, given the benefit of this disclosure.

Example 6

Figure 13:
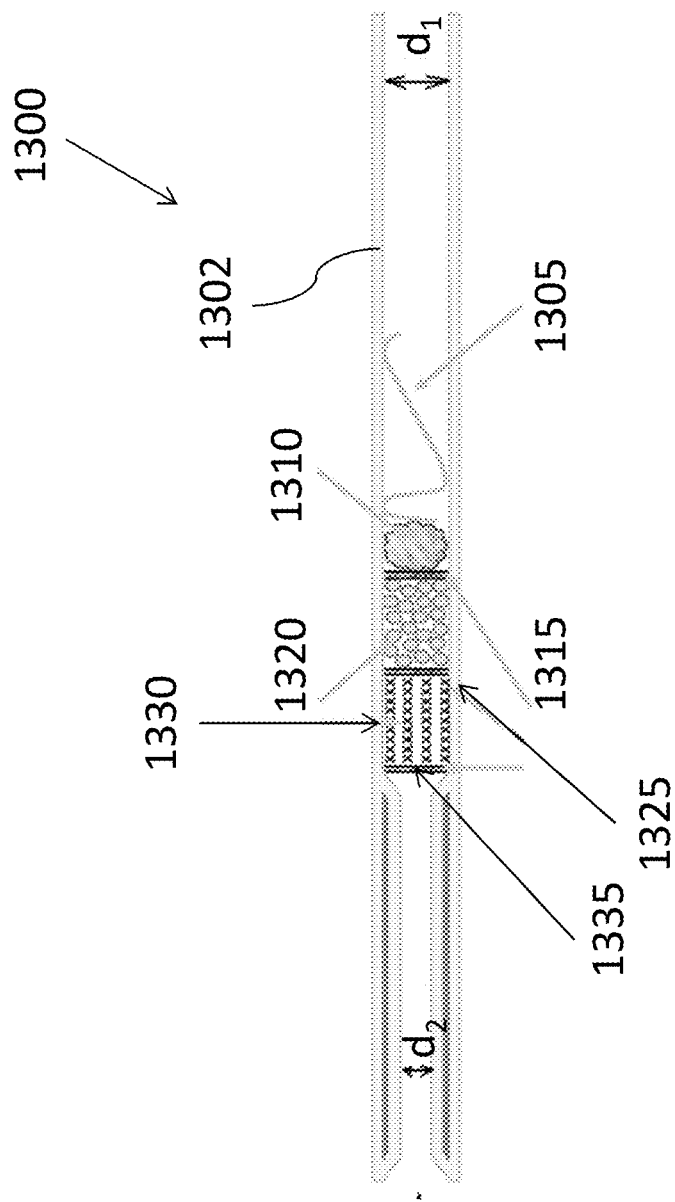
FIG. 13 is an illustration of a sorbent tube comprising differing inner diameters for the inlet and the outlet, in accordance with certain examples.

An illustration of a sorbent tube is shown in FIG. 13. The sorbent tube 1300 comprises a body 1302, which may be glass or stainless steel or other materials. The sorbent tube 1300 is shown as including a clip 1305, glass wool 1310, a steel mesh or screen 1315, glass beads 1320, another steel mesh or screen 1325, a sorbent material 1330, and a third steel mesh or screen 1335. The inner diameter $d_1$ of the inlet of the concentrator trap 1300 is shown as being larger than the inner diameter $d_2$ of the outlet of the concentrator trap 1300. While not wishing to be bound by any scientific theory, the difference in inner diameter may assist in reducing diffusional band broadening. In some instances, the diameter $d_1$ is about 2, 3, 4 or 5 times larger than the diameter $d_2$, e.g., the diameter $d_1$ may be about 2.8 mm and the diameter $d_2$ may be about 0.7 mm.

Example 7

A sorbent tube effective to sample species with a boiling point range from C4 to C44 directly from an air stream can be produced by packing an effective amount of glass beads and sorbent materials into a tube. In one configuration, about 475 mg of glass beads can be placed. The glass beads are placed toward the inlet of the tube. On top of the glass beads, about 350 mg of Carbotrap® C can be placed. On top of the Carbotrap® C, about 200-220 mg of Carbotrap® X can be placed. The glass beads are positioned toward the inlet of the tube, and the Carbotrap® X is positioned toward the outlet of the tube during sampling. If Carbotrap® X is being used, the boiling point range is C4 to C44 and 1,3-butadiene can be retained for analysis.

Example 8

The sorbent tube of Example 7 was used to measure components in a gas stream including C4 to C44 species. In particular, a sample comprising 1,3-butadiene and the aromatics listed above, e.g., BTEX and the EPA regulated PAHs less coronene, was introduced into the sorbent tube of Example 7.

Once the gas stream was drawn into the sorbent tube, chromatographic analysis was performed followed by GC-MS. The thermal desorption parameters and chromatography conditions used are shown in Tables 4 and 5.

TABLE 4

| | |
|---|---|
| Sorbent Tube | Desorb for 15 min @ 380° C. @ 20 mL/min |
| Concentrator Trap | Trap Low 5° C.; Trap high 380° C.; Trap hold 8 min |
| Pneumatics | Inlet split 50 mL/min; Outlet split 20 mL/min; analytical column flow rate 1.0 mL/min |

TABLE 4-continued

| | |
|---|---|
| Ambiet Purge | Purge for 3 min @ ambient temp @ 50 mL/min |
| Transfer Line | 290° C. |
| Valve Temp | 260° C. |
| GC Cyle Time | 16 min |

TABLE 5

| | |
|---|---|
| Oven | 35° C. for 0.5 min; ramp 30° C./min to 185° C.; ramp 10° C./min to 250° C.; ramp 40° C./min 330° C. and hold for 2 min |
| MS Parameters | |
| Mass Range | 35 to 350 amu |
| Source Temp | 270° C. |
| Transfer Line | 290° C. |
| Acquisition | Simultaneous Full Scan and SIM |

Figure 14:
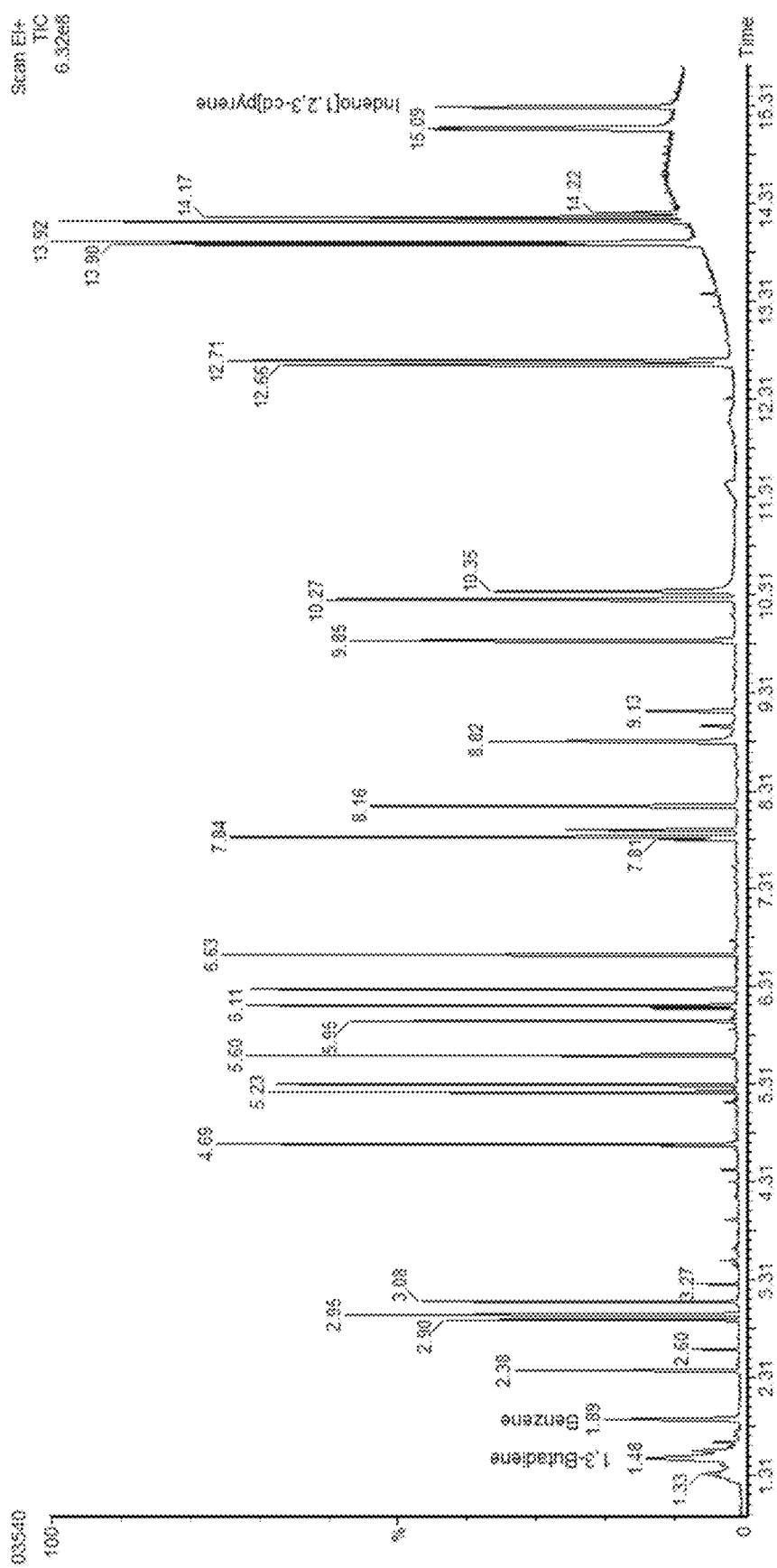
FIG. 14 is a total ion chromatogram showing C4 to C44 species, in accordance with certain examples.

The results of the GC-MS analysis are shown in the total ion chromatogram of FIG. 14. No breakthrough was detected with any of the loaded components.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

The invention claimed is:

1. A method of analyzing a liquefied petroleum gas stream to detect the presence of BTEX and PAHs analytes within a range of C4 to C44 in the liquefied petroleum gas stream, the method comprising:

introducing the liquefied petroleum gas stream into a sorbent tube comprising a plurality of different sorbent materials that together reversibly adsorb each of the BTEX and PAHs analytes within the range of C4 to C44 in the liquefied petroleum gas stream, wherein the liquefied petroleum gas stream is heated and maintained above its bubble point as it is introduced into the sorbent tube, the sorbent tube comprising at least three different sorbent materials packed into the sorbent tube with a sorbent material with a strongest adsorption strength packed closest to an outlet of the sorbent tube and a sorbent material with a weakest adsorption strength packed closest to an inlet of the sorbent tube, wherein each of the at least three different packed sorbent materials is separated from each other by a fluid permeable barrier present between each of the at least three different packed sorbent materials, wherein an entire internal volume of the sorbent tube is occupied by the at least three different packed sorbent materials that are separated by the fluid permeable barrier present between each of the at least three different packed sorbent materials, in which one of the packed sorbent materials comprises glass beads adjacent to the inlet of the sorbent tube, wherein the glass beads comprise a surface area to adsorb BTEX and PAH analyte species with 22 carbons or more in the liquefied petroleum gas stream, and wherein other sorbent materials packed in the sorbent tube together adsorb the BTEX and PAH analytes within a range of C4 to C44 other than the BTEX and PAH analyte species with 22 carbons or more adsorbed by the glass beads, wherein the at least three different packed sorbent materials of the sorbent tube comprise the glass beads adjacent to the inlet of the sorbent tube and at least two different graphitized carbon black materials packed in the sorbent tube with none of the sorbent materials packed in the sorbent tube being the same;

individually and sequentially thermally desorbing each of the adsorbed BTEX and PAH analytes within the range of C4 to C44 from the packed sorbent materials in the sorbent tube using an oven to heat the sorbent tube comprising the BTEX and PAH analytes adsorbed to the at least three different packed sorbent materials in the sorbent tube; and detecting each of the individually and sequentially thermally desorbed BTEX and PAHs analytes by providing each of the individually desorbed BTEX and PAHs analytes to a detector.

2. The method of claim 1, further comprising individually thermally desorbing the adsorbed analytes from the at least three different packed sorbent materials in the sorbent tube using automated thermal desorption.

3. The method of claim 2, further comprising condensing the individually desorbed analytes prior to separation of the desorbed analytes by chromatography.

4. The method of claim 3, further comprising vaporizing the condensed analytes.

5. The method of claim 4, further comprising separating the vaporized analytes using gas chromatography after vaporization of the condensed analytes.

6. The method of claim 5, further comprising sequentially detecting each of the separated, desorbed analytes to determine the amount of each of the BTEX and PAHs analytes within a range of C4 to C44 in the liquefied petroleum gas stream, by providing each of the separated, desorbed analytes to the detector.

7. The method of claim 6, further comprising heating the sorbent tube during the desorbing to remove all the adsorbed BTEX and PAH's analytes within a range of C4 to C44 from the sorbent materials in a single desorption cycle.

8. The method of claim 7, further comprising introducing a carrier gas as a reverse flow during the desorption step.

9. The method of claim 1, further comprising introducing the liquefied petroleum gas stream without any liquid extraction or canister capture of the liquefied petroleum gas stream prior to the introducing step.

10. The method of claim 1, further comprising detecting each of the individually desorbed BTEX and PAHs analytes using a flame ionization detector.

11. The method of claim 10, further comprising providing the individually desorbed BTEX and PAHs analytes to a gas chromatography column to separate the individually desorbed analytes using gas chromatography prior to detecting each of the individually desorbed BTEX and PAHs analytes.

12. The method of claim 1, further comprising drawing the liquefied petroleum gas stream comprising the BTEX and PAHs analytes into the sorbent tube using a pump fluidically coupled to the sorbent tube.

13. The method of claim 1, wherein the at least three different sorbent materials further comprise two or more different glass beads.

14. The method of claim 1, wherein the sorbent tube comprises an internal surface feature comprising caps, chevrons, or fins.

15. The method of claim 1, wherein a mesh size of the each of the packed sorbent materials is 20 to 100 mesh.

16. The method of claim 1, wherein the sorbent tube comprises stationary fluid permeable barrier at one end of the sorbent tube and a clip at another end of the sorbent tube, wherein the clip retains the at least three different packed sorbent materials in the sorbent tube.

* * * * *